(12) United States Patent
Rathi et al.

(10) Patent No.: US 11,485,714 B2
(45) Date of Patent: Nov. 1, 2022

(54) HYDROXYETHYLAMINE-BASED PIPERAZINE COMPOUNDS, AND METHODS OF PRODUCING AND USING THE SAME FOR TREATING DISEASE

(71) Applicant: National Institute of Immunology, New Delhi (IN)

(72) Inventors: Brijesh Rathi, Delhi (IN); Prakasha Kempaiah, Naperville, IL (US); Agam P. Singh, New Delhi (IN); Snigdha Singh, Delhi (IN); Yash Gupta, Forest Park, IL (US); Neha Sharma, Haryana (IN); Poonam, Delhi (IN); Ravi Durvsula, Chicago, IL (US)

(73) Assignee: National Institute of Immunology, New Delhi (IN)

( * ) Notice: Subject to any disclaimer, the term of this patent is extended or adjusted under 35 U.S.C. 154(b) by 0 days.

(21) Appl. No.: 17/347,720

(22) Filed: Jun. 15, 2021

(65) Prior Publication Data

US 2022/0204458 A1 Jun. 30, 2022

(30) Foreign Application Priority Data

Dec. 29, 2020 (IN) .............................. 202011056923

(51) Int. Cl.
 *C07D 295/125* (2006.01)
 *A61P 33/02* (2006.01)
 *C07D 241/04* (2006.01)

(52) U.S. Cl.
 CPC ............ *C07D 241/04* (2013.01); *A61P 33/02* (2018.01); *C07D 295/125* (2013.01)

(58) Field of Classification Search
 CPC .............................. C07D 295/125; A61P 33/02
 See application file for complete search history.

(56) References Cited

PUBLICATIONS

Ciana et al., Bioorganic & Medicinal Chemistry Letters (2013), 23(3), 658-662. (Year: 2013).*

* cited by examiner

*Primary Examiner* — Laura L Stockton
(74) *Attorney, Agent, or Firm* — BakerHostetler

(57) ABSTRACT

Disclosed herein are compounds of Formula (I):

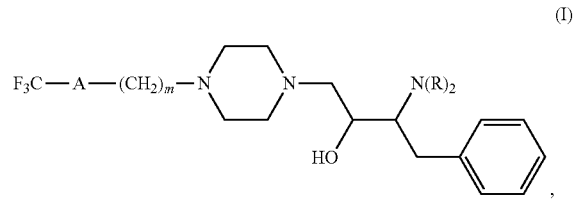

and pharmaceutically acceptable salts thereof, related *pharmaceutical* compositions, and methods for using the same to treat parasitic diseases.

19 Claims, 14 Drawing Sheets

Specification includes a Sequence Listing.

| Agonist | % Aggregation | |
| --- | --- | --- |
| | Saline | Cabimin |
| Saline | 7 | 9 |
| ADP | 62 ± 5 | 68 ± 7 |
| Collagen | 78 ± 8 | 79 ± 6 |
| Epinephrine | 71 ± 4 | 73 ± 5 |
| TRAP | 59 ± 4 | 56 ± 7 |

Fig.11

Most Critical interacting region

Fig. 12

SEQUENCE LISTING

<160> NUMBER OF SEQ ID NOS: 2

<210> SEQ ID NO 1
<211> LENGTH: 1737
<212> TYPE: PRT
<213> ORGANISM: Plasmodium falciparum

<400> SEQUENCE: 1

Met Val Asp Ile Asp Lys Glu Pro Ile Ser Asn Glu Asn Asn Ile Lys
1               5                   10                  15

Tyr Leu Lys Val Tyr Ser Asn Ile Leu Phe Lys Tyr Thr Glu Ala Gln
            20                  25                  30

Glu Lys Lys Lys Glu Tyr Ile Asp Val Ala Leu Leu Gly Asp Asn Ile
        35                  40                  45

```
Lys Glu Glu Lys Arg Phe Phe Lys Leu Ile Asn Ile Asp Ile Ile Leu
 50                  55                  60

Ile Ile Leu Trp Phe Phe Val Leu Tyr Ser Phe Ser Tyr Asn Ile Val
 65                  70                  75                  80

Glu Val Arg Asn Phe Gln Asn Asp Leu Ser Asn Asn Ile Asn Glu Ser
                     85                  90                  95

Thr Phe Tyr Ser Glu Thr Phe Tyr Lys Ser Leu Ser Asp Asn Ile Lys
                100                 105                 110

Lys Ile Asn Asn Asp Tyr Ser Tyr Glu Ser Arg Lys Lys Asp Tyr Thr
                115                 120                 125

Thr Phe Lys Asn Ile Asn Asn Lys Phe Glu Leu Ala Ser Trp Ile Lys
130                 135                 140

Asn Glu Phe Val Lys Asn Val Ser Tyr Glu Lys Tyr Phe Asn Asn
145                 150                 155                 160

Ile Ile Phe Gly Asn Cys Trp Arg Ile Thr Met Arg Leu Tyr Asn Asn
                165                 170                 175

Asn Asn Asn Asn Asn Asn Ser Asn Asp Ser Leu Ile Lys Lys Ile Tyr
                180                 185                 190

Asn Lys Lys Lys Leu Tyr Glu Ile Tyr Ser Asp Thr Asn Phe Leu Lys
                195                 200                 205

Glu Ile Glu Asn Lys Gln Asn Ile Ser Tyr Pro Tyr Phe Asp Lys Lys
                210                 215                 220

Trp Asn Tyr Asn Phe Ser Tyr Glu Lys Ser Tyr Lys Lys Ile Gly Gly
225                 230                 235                 240

Leu Tyr Gln Ile Ile Cys Glu Asn Asp Tyr Asn Lys Ile Gln Glu Met
                245                 250                 255

Leu Ser Gln Asn Ser Phe Tyr Thr Thr Ser Tyr Pro Tyr Phe Ile Pro
                260                 265                 270

Ala Val Ile Leu Thr Asn Tyr Asn Ile Ala Thr Val Thr Leu Asp Tyr
                275                 280                 285

Leu Leu Tyr Asn Pro Ile Leu Asn Leu Ile Ser Tyr Asn Ala Leu Lys
                290                 295                 300

Phe Ser Phe Leu Pro Asn Thr Lys Thr Tyr Lys Glu Ile Val Thr Leu
305                 310                 315                 320

Ser Ala Ser Cys Asn Gln Ile Asn Leu Tyr Phe Val Val Ser Phe Phe
                325                 330                 335

Val Phe Leu Cys Ile Phe Ile Thr Tyr Ile Leu Lys Asp Val Arg Thr
                340                 345                 350

Tyr Phe Leu Val Gly Phe Asn Leu Tyr Val Lys Thr Tyr Ser Cys Lys
                355                 360                 365

Phe Met Ile Ile Val Cys Val Leu Leu Asn Met Leu Ser Leu Gly Ile
                370                 375                 380

Tyr Val Leu Phe Gln Tyr Lys Val Pro Asn Leu Asn Ala Thr Tyr Glu
385                 390                 395                 400

Asn Gly Lys Tyr Lys Ile Asp Ser Leu Tyr Ala Asn Ala Asn Ser Glu
                405                 410                 415

Ser Ile Val Asn Met Phe Tyr Asp Ile Glu Arg Val Ile Leu Tyr Ile
                420                 425                 430

Glu Trp Thr Lys Tyr Ile Phe Ile Phe Thr Cys Phe Ile Thr Phe Ile
                435                 440                 445

Phe Ser Tyr Tyr Leu Ile Ile Lys Asn Tyr Gly Leu Leu Ile Lys Lys
450                 455                 460
```

-continued

```
Tyr Asn Asn Val Glu Lys Asn Ile Lys Lys Asp Phe Leu Tyr Pro Cys
465                 470                 475                 480

Ser Ile Leu Leu Ile Val Val Phe Ile Tyr Leu Cys Ile Val Ser Met
            485                 490                 495

Tyr Arg Tyr Glu Val Phe Asn Ile Phe Glu Asn Glu Asn Cys Asn Met
                500                 505                 510

Leu Tyr Ala Tyr Ile Leu Asn Ile Cys Leu Val Phe Ala Asn Phe Gln
            515                 520                 525

Gly Phe Asn Ile Ser Ser Ile Ile Asn Ala Glu Gly Asn Asn Leu Pro
    530                 535                 540

Tyr Phe Tyr Phe Ile Pro Thr Leu Phe Phe Ile Phe Thr Ile Ile Phe
545                 550                 555                 560

Ser Phe Ile Phe Phe Leu Ala Ile Lys Ser Tyr Ile Lys Arg Asn Lys
                565                 570                 575

Lys Met Tyr Lys Trp Tyr Met Arg His Phe Lys Asp Asn Arg Pro Leu
            580                 585                 590

Ser Lys Asp Asn Asn Thr Glu Lys Gly Ile Lys Ile Arg Ala Tyr Lys
    595                 600                 605

Lys Arg Lys Ser Ile Tyr Asn Lys Asn Asn Glu Tyr Asn Lys Ser Glu
            610                 615                 620

Arg Thr Val Glu Thr Asn Ile Cys Asn Asp Glu Arg Ser Gln Asn Glu
625                 630                 635                 640

Ile Lys Lys Glu Lys Thr Lys Glu Lys Ile Glu Lys Asn Glu Asn Glu
                645                 650                 655

Lys Gln Gly Glu Thr Gln Lys Glu Asn Ile Lys Asp Glu Asn Ile Lys
            660                 665                 670

Asp Glu Tyr Ile Gln Asp Glu Tyr Ile Gln Asp Glu Tyr Ile Gln Asp
    675                 680                 685

Glu Tyr Ile Lys Asp Glu Tyr Ile Lys Asp Glu Asp Ile Gln Asp Glu
690                 695                 700

Asp Ile Gln Asp Glu Asp Ile Gln Asp Gln Asn Ile His Asp Gln Asn
705                 710                 715                 720

Ile His Asp Gln Asn Thr His Asn Arg Lys Gly Asn Asn Lys Asn Ile
                725                 730                 735

Tyr His Asn Lys Ser His His Lys Asn Ile His Asn Asn Asn Thr Val
            740                 745                 750

Glu Tyr Asn Ser Glu Glu Asp Gly Asn Ser Lys Ser Lys Leu Ser Lys
    755                 760                 765

Asp Leu Pro Leu Ser Asp Leu Lys Glu Asp Thr Ile Lys Asn Asn Asn
770                 775                 780

Ser Asn Thr Ser Lys Asn Ser Tyr Asp Asn Ser Glu Glu Asn Asn Ile
785                 790                 795                 800

Arg Asn Val Glu Tyr Met Asn Glu Asp Gly Ser Glu Cys Tyr Asn Phe
                805                 810                 815

Pro Leu Asn Asn Ser Ser Asp Cys Glu Ile Asn Val Asp Asn Ile Asp
            820                 825                 830

Lys Glu Leu Asn Tyr Lys Asp Ile Ile Lys Leu Gly Lys Lys Ser Asn
    835                 840                 845

Thr Asn Lys Glu Val Tyr Ser Ser Asn Met Met Glu Glu Asn Glu Glu
850                 855                 860

Asn Ile Phe Gln Ile Glu Lys Phe Ile Asn Ile Phe Asn Leu Arg
                865                 870                 875                 880

Asn Arg Phe Leu Pro Phe Ser Tyr Asn Val Lys Lys Tyr Ile Leu Lys
```

```
                    885                 890                 895
Glu Tyr Asn Lys Lys Thr Lys Asn Lys Lys Ser Glu Lys Leu Ile Cys
                900                 905                 910

Phe Phe Tyr Ile Phe Met Gly Leu Leu Ile Phe Cys Ser Leu Phe Ile
                915                 920                 925

Ile Asn Asn Phe Lys Lys Ile Ser Glu Thr Glu Asn Leu Leu Lys Tyr
                930                 935                 940

Gln Ile Glu Asn Val Ser Tyr Leu Ser Ser Asp Lys Leu Phe Thr Asn
945                 950                 955                 960

Met Lys Phe Tyr His Glu Asn Lys Ser Leu Asn Val Ser Ile Asn Asn
                965                 970                 975

Glu Tyr Leu Asn Phe His Lys Ile Lys Asn Lys Asn Asp Ile Ile Glu
                980                 985                 990

Trp Ile Lys Asn Cys Phe Pro Val Tyr Leu Glu Asn Gly Thr Asp Leu
                995                 1000                1005

Phe Gly Asn Asn Ala Ile Tyr His Asn Ser Tyr Lys Trp Ile Glu
            1010                1015                1020

Ile Tyr Asp Leu Leu Tyr Gly Lys Ile Tyr Ile Arg Met Thr Ser
            1025                1030                1035

Arg Glu Glu Ile Asn Ile Ser Asp Asn Leu Asn Asn Asn Asn Asn
            1040                1045                1050

Asn Asn Asn Asn Asn Asn Ile Ile Cys Asn Asn Arg Gln Asp
            1055                1060                1065

Lys Cys Tyr Ala Tyr Ile Arg Asn Glu Lys Asn Ile Leu Lys Asn
            1070                1075                1080

Asn Leu Asn Asp Ile Leu Ser Leu Ile Asp Asp Ser Ile Lys Glu
            1085                1090                1095

Leu Glu Ile Ser Phe Ile Leu Ser Asp Val Asp Asp His His Asn
            1100                1105                1110

Ile Leu Val Lys Ile Asn Phe His Phe Thr Ser Thr Gly Tyr Ile
            1115                1120                1125

Ser Lys Tyr Ile Gln Phe Asp His Leu Phe Phe Asn Ser Phe Asn
            1130                1135                1140

Ile Tyr Gln Phe Ile Gly Val Val Asn Phe Leu Tyr Leu Ile
            1145                1150                1155

Ile Leu Leu Ser Leu Leu Ile Val Ile Tyr Lys Tyr Tyr Tyr Thr
            1160                1165                1170

Asn Phe Phe Tyr Phe Tyr Asn Leu Cys Val Ser Ser Leu Lys Gly
            1175                1180                1185

Thr Ile His Ser Asn Asn Ser Asn Met Thr His Ile Met Asn Thr
            1190                1195                1200

Gln Met Glu Asn Phe Met Tyr Arg Asn Asp Asn Asn Arg Arg Asn
            1205                1210                1215

Leu Gln Asn Met Asp Asn Ala Asn Asn Phe Asn Val Val Asn Ile
            1220                1225                1230

Asn Asn Asn Asn Asn Asn Asp Asn Ser Asn Ser Tyr Ser Tyr Gly
            1235                1240                1245

Asn Asn Ile Met Phe Asp Lys Tyr Lys Asp Asn Asn Met Asn Asn
            1250                1255                1260

Glu Glu Ile Asn Tyr Tyr Gly Pro Tyr Tyr Asn Glu Asn Asn Phe
            1265                1270                1275

Thr Leu Asn Asn Asn Tyr Ile Ser Asn Met Asn Tyr His Pro Asp
            1280                1285                1290
```

-continued

```
Asn Phe Tyr Ser Asn Ala Asn Ile Asn Asn Lys Thr Thr Lys Tyr
    1295                1300                1305

Asn Leu Ser Leu Leu Leu His Leu Lys Ile Tyr Leu Thr Tyr Leu
    1310                1315                1320

Phe Glu Cys Asp Ile Ile Lys Leu Phe Ile Phe Ile Leu His Ile
    1325                1330                1335

Leu Ile Val Leu Phe Trp Leu Ala Leu Cys Ile Asn Ile Asn Arg
    1340                1345                1350

Ile Ser Tyr Tyr Asn Glu Ile Leu Leu Asp Ser Tyr Phe Asp Ile
    1355                1360                1365

His Ile Asn Thr Ile Ser Phe Tyr Ser Ile Met Ile Tyr Ile Phe
    1370                1375                1380

Tyr Leu Phe Leu Phe Leu Thr Ile Met Asn Met Phe Phe Tyr Leu
    1385                1390                1395

Ser Lys Tyr Val Lys Asn Glu Val Ile Tyr Glu Ala Leu Tyr Tyr
    1400                1405                1410

Asn Arg Leu Gln Ile Leu Lys Ser Val Leu Leu Leu Leu Phe Val
    1415                1420                1425

Cys Phe His Phe Ile Ile Phe His Tyr Phe Phe Tyr Tyr Gly Ile
    1430                1435                1440

Asp Asn Tyr Gln Asn Leu Thr Ile Tyr Glu His Val Ile Tyr Ser
    1445                1450                1455

Phe Leu Ile Leu Ile Gly Met Val Lys Met Glu Ile Tyr Leu Lys
    1460                1465                1470

Tyr Ser Thr Leu Tyr Phe Phe Val Ile Ile Leu Pro His Leu Ile
    1475                1480                1485

Phe Ile Arg Phe Leu Phe Ile Tyr Thr Leu Phe Ala Pro Ile Leu
    1490                1495                1500

Ser Ser Tyr Ile Ile Lys Lys Asn Arg Ser Lys Gln Ser Asn
    1505                1510                1515

Asn Thr Asp Asn Ile Ser Ser Asp Lys Val Tyr Asn Ile Glu Ser
    1520                1525                1530

Asn Tyr Gly Asp Ser Ser Met Tyr Asn Met Glu Asn Met Asn Thr
    1535                1540                1545

Asp Phe Met Tyr Asn Ile Asp Asn Asn Asn Asn Lys Lys Lys
    1550                1555                1560

Asn Ser Asn Asn Asn Asn Asp Ile Lys Asn Asn Asn Lys Asn
    1565                1570                1575

Asn Asn Lys Arg Asn Leu Ile Tyr Lys Glu Gln Lys Glu Asn Asp
    1580                1585                1590

Thr Asn Asn Gln Tyr Asp Glu Glu Asp Tyr Lys Ala Phe Ile Leu
    1595                1600                1605

Thr Arg Leu Ser Ser Glu Gln Trp Lys Gly Leu Lys Glu Glu Ile
    1610                1615                1620

Lys Glu Phe Ala Lys Met Glu Thr Tyr Asn Ile Leu Val Tyr Phe
    1625                1630                1635

Gln Lys Phe Lys Asn Gln Ile Asp Ser Lys Lys Ile Asn Phe Met
    1640                1645                1650

Ser Thr Ile Leu Lys Asn Glu Tyr Thr Tyr Leu Asn Glu Gln Ile
    1655                1660                1665

Asn Asn Ile Ile Leu Asp Leu Arg Lys Val Glu Leu Gln Trp Lys
    1670                1675                1680
```

```
Phe Gln Ser Lys Leu Val Asn Ser Ser Asn Ala Tyr Ile Asp Lys
    1685                1690                1695

Ile Asn Asn Gln Ile Asp Met Asn Glu Glu Ile Val Glu Ser
    1700                1705                1710

Lys Ser Lys Leu Ser Ser Leu Lys Gln Tyr Leu Gln Lys Val Gln
    1715                1720                1725

Met Asp Pro Thr Lys Glu Arg Asp Glu
    1730                1735

<210> SEQ ID NO 2
<211> LENGTH: 1373
<212> TYPE: PRT
<213> ORGANISM: Plasmodium falciparum

<400> SEQUENCE: 2

Ser Asn Asp Ser Leu Ile Lys Lys Ile Tyr Asn Lys Lys Leu Tyr
1               5                   10                  15

Glu Ile Tyr Ser Asp Thr Asn Phe Leu Lys Glu Ile Glu Asn Lys Gln
                20                  25                  30

Asn Ile Ser Tyr Pro Tyr Phe Asp Lys Lys Trp Asn Tyr Asn Phe Ser
            35                  40                  45

Tyr Glu Lys Ser Tyr Lys Lys Ile Gly Gly Leu Tyr Gln Ile Ile Cys
    50                  55                  60

Glu Asn Asp Tyr Asn Lys Ile Gln Glu Met Leu Ser Gln Asn Ser Phe
65                  70                  75                  80

Tyr Thr Thr Ser Tyr Pro Tyr Phe Ile Pro Ala Val Ile Leu Thr Asn
                85                  90                  95

Tyr Asn Ile Ala Thr Val Thr Leu Asp Tyr Leu Leu Tyr Asn Pro Ile
            100                 105                 110

Leu Asn Leu Ile Ser Tyr Asn Ala Leu Lys Phe Ser Phe Leu Pro Asn
        115                 120                 125

Thr Lys Thr Tyr Lys Glu Ile Val Thr Leu Ser Ala Ser Cys Asn Gln
    130                 135                 140

Ile Asn Leu Tyr Phe Val Val Ser Phe Phe Val Phe Leu Cys Ile Phe
145                 150                 155                 160

Ile Thr Tyr Ile Leu Lys Asp Val Arg Thr Tyr Phe Leu Val Gly Phe
                165                 170                 175

Asn Leu Tyr Val Lys Thr Tyr Ser Cys Lys Phe Met Ile Ile Val Cys
            180                 185                 190

Val Leu Leu Asn Met Leu Ser Leu Gly Ile Tyr Val Leu Phe Gln Tyr
        195                 200                 205

Lys Val Pro Asn Leu Asn Ala Thr Tyr Glu Asn Gly Lys Tyr Lys Ile
    210                 215                 220

Asp Ser Leu Tyr Ala Ala Asn Ser Glu Ser Ile Val Asn Met Phe
225                 230                 235                 240

Tyr Asp Ile Glu Arg Val Ile Leu Tyr Ile Glu Trp Thr Lys Tyr Ile
                245                 250                 255

Phe Ile Phe Thr Cys Phe Ile Thr Phe Ile Phe Ser Tyr Tyr Leu Ile
            260                 265                 270

Ile Lys Asn Tyr Gly Leu Leu Ile Lys Lys Tyr Asn Asn Val Glu Lys
        275                 280                 285

Asn Ile Lys Lys Asp Phe Leu Tyr Pro Cys Ser Ile Leu Leu Ile Val
    290                 295                 300

Val Phe Ile Tyr Leu Cys Ile Val Ser Met Tyr Arg Tyr Glu Val Phe
305                 310                 315                 320
```

-continued

```
Asn Ile Phe Glu Asn Glu Asn Cys Asn Met Leu Tyr Ala Tyr Ile Leu
                325                 330                 335
Asn Ile Cys Leu Val Phe Ala Asn Phe Gln Gly Phe Asn Ile Ser Ser
            340                 345                 350
Ile Ile Asn Ala Glu Gly Asn Asn Leu Pro Tyr Phe Tyr Phe Ile Pro
        355                 360                 365
Thr Leu Phe Phe Ile Phe Thr Ile Ile Phe Ser Phe Ile Phe Phe Leu
    370                 375                 380
Ala Ile Lys Ser Tyr Ile Lys Arg Asn Lys Lys Met Tyr Lys Trp Tyr
385                 390                 395                 400
Met Arg His Phe Lys Asp Asn Arg Pro Leu Ser Lys Asp Asn Asn Thr
                405                 410                 415
Glu Lys Gly Ile Lys Ile Arg Ala Tyr Lys Lys Arg Lys Ser Ile Tyr
            420                 425                 430
Asn Lys Asn Asn Glu Tyr Asn Lys Ser Glu Arg Thr Val Glu Thr Asn
        435                 440                 445
Ile Cys Asn Asp Glu Arg Ser Gln Asn Glu Ile Lys Lys Glu Lys Thr
    450                 455                 460
Lys Glu Lys Ile Glu Lys Asn Glu Asn Glu Lys Gln Gly Glu Thr Gln
465                 470                 475                 480
Lys Glu Asn Ile Lys Asp Glu Asn Ile Lys Asp Glu Tyr Ile Gln Asp
                485                 490                 495
Glu Tyr Ile Gln Asp Glu Tyr Ile Gln Asp Glu Tyr Ile Lys Asp Glu
            500                 505                 510
Tyr Ile Lys Asp Glu Asp Ile Gln Asp Glu Asp Ile Gln Asp Glu Asp
        515                 520                 525
Ile Gln Asp Gln Asn Ile His Asp Gln Asn Ile His Asp Gln Asn Thr
    530                 535                 540
His Asn Arg Lys Gly Asn Asn Lys Asn Ile Tyr His Asn Lys Ser His
545                 550                 555                 560
His Lys Asn Ile His Asn Asn Thr Val Glu Tyr Asn Ser Glu Glu
                565                 570                 575
Asp Gly Asn Ser Lys Ser Lys Leu Ser Lys Asp Leu Pro Leu Ser Asp
            580                 585                 590
Leu Lys Glu Asp Thr Ile Lys Asn Asn Ser Asn Thr Ser Lys Asn
                595                 600                 605
Ser Tyr Asp Asn Ser Glu Glu Asn Asn Ile Arg Asn Val Glu Tyr Met
    610                 615                 620
Asn Glu Asp Gly Ser Glu Cys Tyr Asn Phe Pro Leu Asn Asn Ser Ser
625                 630                 635                 640
Asp Cys Glu Ile Asn Val Asp Asn Ile Asp Lys Glu Leu Asn Tyr Lys
                645                 650                 655
Asp Ile Ile Lys Leu Gly Lys Lys Ser Asn Thr Asn Lys Glu Val Tyr
            660                 665                 670
Ser Ser Asn Met Met Glu Glu Asn Glu Asn Ile Phe Gln Ile Glu
        675                 680                 685
Lys Phe Ile Asn Ile Phe Phe Asn Leu Arg Asn Arg Phe Leu Pro Phe
    690                 695                 700
Ser Tyr Asn Val Lys Lys Tyr Ile Leu Lys Glu Tyr Asn Lys Lys Thr
705                 710                 715                 720
Lys Asn Lys Lys Ser Glu Lys Leu Ile Cys Phe Phe Tyr Ile Phe Met
                725                 730                 735
```

-continued

Gly Leu Leu Ile Phe Cys Ser Leu Phe Ile Ile Asn Asn Phe Lys Lys
                740                 745                 750

Ile Ser Glu Thr Glu Asn Leu Leu Lys Tyr Gln Ile Glu Asn Val Ser
            755                 760                 765

Tyr Leu Ser Ser Asp Lys Leu Phe Thr Asn Met Lys Phe Tyr His Glu
    770                 775                 780

Asn Lys Ser Leu Asn Val Ser Ile Asn Asn Glu Tyr Leu Asn Phe His
785                 790                 795                 800

Lys Ile Lys Asn Lys Asn Asp Ile Ile Glu Trp Ile Lys Asn Cys Phe
                805                 810                 815

Pro Val Tyr Leu Glu Asn Gly Thr Asp Leu Phe Gly Asn Asn Ala Ile
            820                 825                 830

Tyr His Asn Ser Tyr Lys Trp Ile Glu Ile Tyr Asp Leu Leu Tyr Gly
                835                 840                 845

Lys Ile Tyr Ile Arg Met Thr Ser Arg Glu Glu Ile Asn Ile Ser Asp
            850                 855                 860

Asn Leu Asn Asn Asn Asn Asn Asn Asn Asn Asn Asn Asn Asn Ile Ile
865                 870                 875                 880

Cys Asn Asn Arg Gln Asp Lys Cys Tyr Ala Tyr Ile Arg Asn Glu Lys
                885                 890                 895

Asn Ile Leu Lys Asn Asn Leu Asn Asp Ile Leu Ser Leu Ile Asp Asp
            900                 905                 910

Ser Ile Lys Glu Leu Glu Ile Ser Phe Ile Leu Ser Asp Val Asp Asp
            915                 920                 925

His His Asn Ile Leu Val Lys Ile Asn Phe His Phe Thr Ser Thr Gly
            930                 935                 940

Tyr Ile Ser Lys Tyr Ile Gln Phe Asp His Leu Phe Phe Asn Ser Phe
945                 950                 955                 960

Asn Ile Tyr Gln Phe Ile Gly Val Val Asn Phe Leu Tyr Leu Ile
                965                 970                 975

Ile Leu Leu Ser Leu Leu Ile Val Ile Tyr Lys Tyr Tyr Tyr Thr Asn
            980                 985                 990

Phe Phe Tyr Phe Tyr Asn Leu Cys Val Ser Ser Leu Lys Gly Thr Ile
    995                 1000                1005

His Ser Asn Asn Ser Asn Met Thr His Ile Met Asn Thr Gln Met
    1010                1015                1020

Glu Asn Phe Met Tyr Arg Asn Asp Asn Arg Arg Asn Leu Gln
    1025                1030                1035

Asn Met Asp Asn Ala Asn Asn Phe Asn Val Val Asn Ile Asn Asn
    1040                1045                1050

Asn Asn Asn Asn Asp Asn Ser Asn Ser Tyr Ser Tyr Gly Asn Asn
    1055                1060                1065

Ile Met Phe Asp Lys Tyr Lys Asp Asn Asn Met Asn Asn Glu Glu
    1070                1075                1080

Ile Asn Tyr Tyr Gly Pro Tyr Tyr Asn Glu Asn Asn Phe Thr Leu
    1085                1090                1095

Asn Asn Asn Tyr Ile Ser Asn Met Asn Tyr His Pro Asp Asn Phe
    1100                1105                1110

Tyr Ser Asn Ala Asn Ile Asn Asn Lys Thr Thr Lys Tyr Asn Leu
    1115                1120                1125

Ser Leu Leu Leu His Leu Lys Ile Tyr Leu Thr Tyr Leu Phe Glu
    1130                1135                1140

Cys Asp Ile Ile Lys Leu Phe Ile Phe Ile Leu His Ile Leu Ile

```
                1145                1150                1155
Val Leu Phe Trp Leu Ala Leu Cys Ile Asn Ile Asn Arg Ile Ser
                1160                1165                1170
Tyr Tyr Asn Glu Ile Leu Leu Asp Ser Tyr Phe Asp Ile His Ile
                1175                1180                1185
Asn Thr Ile Ser Phe Tyr Ser Ile Met Ile Tyr Ile Phe Tyr Leu
                1190                1195                1200
Phe Leu Phe Leu Thr Ile Met Asn Met Phe Phe Tyr Leu Ser Lys
                1205                1210                1215
Tyr Val Lys Asn Glu Val Ile Tyr Glu Ala Leu Tyr Tyr Asn Arg
                1220                1225                1230
Leu Gln Ile Leu Lys Ser Val Leu Leu Leu Phe Val Cys Phe
                1235                1240                1245
His Phe Ile Ile Phe His Tyr Phe Phe Tyr Tyr Gly Ile Asp Asn
                1250                1255                1260
Tyr Gln Asn Leu Thr Ile Tyr Glu His Val Ile Tyr Ser Phe Leu
                1265                1270                1275
Ile Leu Ile Gly Met Val Lys Met Glu Ile Tyr Leu Lys Tyr Ser
                1280                1285                1290
Thr Leu Tyr Phe Phe Val Ile Ile Leu Pro His Leu Ile Phe Ile
                1295                1300                1305
Arg Phe Leu Phe Ile Tyr Thr Leu Phe Ala Pro Ile Leu Ser Ser
                1310                1315                1320
Tyr Ile Ile Ile Lys Lys Asn Arg Ser Lys Gln Ser Asn Asn Thr
                1325                1330                1335
Asp Asn Ile Ser Ser Asp Lys Val Tyr Asn Ile Glu Ser Asn Tyr
                1340                1345                1350
Gly Asp Ser Ser Met Tyr Asn Met Glu Asn Met Asn Thr Asp Phe
                1355                1360                1365
Met Tyr Asn Ile Asp
                1370
```

HYDROXYETHYLAMINE-BASED PIPERAZINE COMPOUNDS, AND METHODS OF PRODUCING AND USING THE SAME FOR TREATING DISEASE

CROSS-REFERENCE TO RELATED APPLICATIONS

The instant application claims the benefit of priority of Indian patent application no. 202011056923 filed Dec. 29, 2020, the content of which is incorporated by reference in its entirety.

SEQUENCE LISTING

The instant application contains a Sequence Listing which has been submitted electronically in ASCII format and is hereby incorporated by reference in its entirety. Said ASCII copy, created on Mar. 15, 2022, is named 94735_22120_SL.txt and is 27,439 bytes in size.

TECHNICAL FIELD OF INVENTION

The present invention provides novel compounds of formula I, pharmaceutically acceptable salts thereof, pharmaceutical compositions thereof and method for the treatment and prevention of malaria infection and transmission in a mammal. In particular, the present disclosure relates to hydroxyethylamine-based compounds, and their use for treating protozoan parasitic diseases, such as malaria.

BACKGROUND OF INVENTION

Parasitic infections are a global threat in human and animal populations. Due to widespread drug resistance and limited alternatives, protozoan parasite infections have become harder to combat. There are five main parasites belonging to the Apicomplexans and Kinetoplastids groups, namely *Plasmodium falciparum, Leishmania* Spp., *Trypanosoma cruzi. Toxoplasma gondii*, and Crypiosporidium spp. *Plasmodium. Toxoplasma*, and Cryplosporidium belong to the phylum Apicomplexa, while Typanosoma and *Leishmania* are flagellated protozoans grouped under Kinetoplastids. The global incidence of these protozoan parasites is alarming, together affecting over half the world's population (CDC 2018 Content source: Global Health, Division of Parasitic Diseases and Malaria. WHO-Malaria report 2019 who.int/publications-detaillworld-malaria-report-2019). Specifically, malaria caused by parasites of the genus *Plasmodium* continues to be a major global health threat with endemicity in over 100 countries and more than 3.4 billion people still at risk. Despite making considerable progress in malaria control and reduction efforts through awareness, mass spraying and use of insecticide treated bed nets, malaria cases are still on raise. Recently, RTS,S, the first malaria vaccine for children living in *P. falciparum* endemic areas was approved. However, its applicability is limited due to its partial protection efficacy and requirement of multiple boosters. Currently, malaria control relies heavily on the administration of effective antimalarials. Although artemisinin combination therapies ("ACTs") are the first line of treatment, emergence and rapid spread of ACT- and multi-drug resistant ("MDR") strains in many endemic regions albeit sparing sub-Saharan regions, creates serious challenges. Therefore, the emergence of drug resistance coupled with the limited availability of alternate therapeutic options creates an urgent need to discover novel and effective antimalarials targeting essential parasite pathways with reduced toxicity to the host.

Leishmaniasis is recognized by the World Health Organization (WHO) as one of the six tropical diseases of greatest importance to man. In 2017, there were 22,415 new leishmaniasis cases reported, with 94% of these cases occurring in Brazil, Ethiopia, India, Kenya. Somalia, Sudan, and South Sudan (WHO-*Leishmania* report: https://www.who.int/leishmaniasis/en/;who.int/news-room/fact-sheets/detail/leishmaniasis; cdc.sov/parasites/leishmaniasis/index.html).

Although substantial progress in global vector and parasite control has been achieved with a significant reduction in mortality, these important gains are contingent on effective therapeutics. Currently, the best methods for the control of many insects and contaminated food borne diseases involve chemicals and pesticides. Using these approaches, malaria was nearly eliminated from the Indian subcontinent and Chagas disease is rapidly being vanquished in some sections of Central and South America. Moreover, a key strategy for reducing leishmaniasis incidence is controlling sandflies (the vector of *Leishmania* spp. parasites) through insecticide and bed net use. However, this has proven challenging.

Due to widespread drug resistance and limited alternatives, protozoan parasite infections have become harder to combat and thus, new and targeted therapeutics are needed. Particularly, effective malaria control is severely impeded by therapeutics rendered ineffective due to resistance, their prohibitive costs, and cumulative toxic effects. Compounds capable of treating protozoan parasitic diseases, such as multi-stage antimalarials, with novel mechanisms of action are needed to broaden the therapeutic scope and to overcome resistance to frontline therapeutics.

SUMMARY OF INVENTION

In one aspect, disclosed herein are compounds of Formula (I):

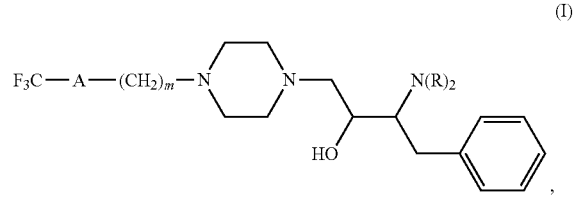

and pharmaceutically acceptable salts thereof, wherein A is $C_{6-10}$aryl; each R independently is H or $CH_3$; and m is 1, 2, or 3. In some cases, A is $C_{6-10}$aryl. In some embodiments, A is phenyl or naphthyl. In various cases, A is phenyl. In various embodiments, $CF_3$-A is

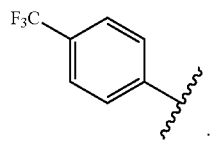

In some embodiments each R is H. In various embodiments, each R is $CH_3$. In some cases, one R is H and one R is CH$_3$. In various cases, m is 1. In some cases, m is 2. In various embodiments, m is 3. In some cases, CF$_3$-A is

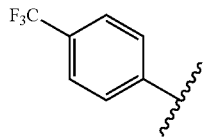 [SMILES: *c1ccc(C(F)(F)F)cc1]

and m is 1.

In various cases, the compound of Formula (I) has a structure of Compound (I) Calxinin:

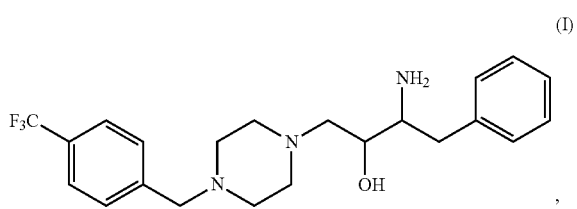 [SMILES: NC(Cc1ccccc1)C(O)CN1CCN(Cc2ccc(C(F)(F)F)cc2)CC1]

(I)

or a pharmaceutically acceptable salt thereof. In some cases, the compound of Formula (I) or pharmaceutically acceptable salt thereof exhibits stereochemistry, as shown in Compound Ia:

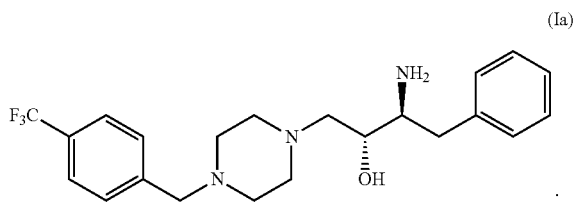 [SMILES: N[C@@H](Cc1ccccc1)[C@H](O)CN1CCN(Cc2ccc(C(F)(F)F)cc2)CC1]

(Ia)

Another aspect of the disclosure provides a pharmaceutical composition comprising the compound and pharmaceutically acceptable salts disclosed herein and a pharmaceutically acceptable excipient.

Yet another aspect of the disclosure provides a method of treating a protozoan parasitic disease in a subject comprising administering to the subject a therapeutically effective amount of a compound or pharmaceutically acceptable salt described herein, or a pharmaceutically acceptable composition described herein. In some embodiments, the protozoan parasitic disease is malaria, Leishmaniasis, Toxoplasmosis, Chagas, or Cryptosporidiosis. In various embodiments, the protozoan parasitic disease is malaria or Leishmaniasis. In some cases, the protozoan parasitic disease is malaria. In various cases, the malaria is liver stage malaria. In some embodiments, the malaria is blood stage malaria. In various embodiments, the malaria is gametocyte and/or ookinete stage malaria. In some cases, the subject is infected with a malaria-causing parasite. In various cases, malaria-causing parasite is *Plasmodium folciparum*, *Plasmodium vivax*, *Plasmodium ovale curtisi*, *Plasmodium knowlesi*, *Plasmodium berghei*, or *Plasmodium malariae*. In some embodiments, the *Plasmodium falciparum* or *Plasmodium berghei* parasite is resistant to chloroquine ("CQ"), artemisinin ("ART"), dihydroartemisinin ("DHA"), or combinations thereof. In various cases, the protozoan parasitic disease is Leishmaniasis. In some embodiments, the subject is infected with a Leishmaniasis-causing parasite. In various embodiments, the Leishmaniasis-causing parasite is *Leishmania donovani*, *Leishmania major*, *Leishmania tropica*, *Leishmania braziliensis*, *Leishmania mexicana*, *Leishmania amazonensis*, or *Leishmania Chagasi*. In some cases, the protozoan parasitic disease is Toxoplasmosis. In various cases, the subject is infected with a Toxoplasmosis-causing parasite. In some embodiments, the Toxoplasmosis-causing parasite is *Toxoplasma gondii*. In some cases, the protozoan parasitic disease is Chagas. In various cases, the subject is infected with a Chagas-causing parasite. In some embodiments, the Chagras-causing parasite is *Trypanosoma cruzi*. In various embodiments, the disease is African sleeping sickness. In some cases, the protozoan parasitic disease is Cryptosporidiosis. In various cases, the subject is infected with a Cryptosporidiosis-causing parasite. In some embodiments, the Cryptosporidiosis-causing parasite is *Cryptosporidium parvum* and *Cryptosporidium hominis*.

In various embodiments, the compound disclosed herein or the composition disclosed herein is administered in combination with another anti-parasitic therapeutic. In some cases, the other anti-parasitic therapeutic is selected from the group consisting of quinine, chloroquine ("CQ"), proguanil, sulfadoxine-pyrimethamine, mefloquine, atovaguone, doxycycline ("DOX"), clindamycin, artemisinin, and dihydroartemisinin ("DHA"). In various cases, the other anti-parasitic therapeutic is dihydroartemisinin ("DHA").

Further aspects and advantages will be apparent to those of ordinary skill in the art from a review of the following detailed description, taken in conjunction with the drawings. While the compounds and methods disclosed herein are susceptible of embodiments in various forms, the description hereafter includes specific embodiments with the understanding that the disclosure is illustrative, and is not intended to limit the invention to the specific embodiments described herein.

DRAWINGS

The foregoing summary, as well as the following detailed description of the invention will be better understood when read in conjunction with the appended drawings. For the purpose of assisting in the explanation of the invention, there are shown in the drawings embodiments which are presently preferred and considered illustrative. It should be understood, however, that the invention is not limited to the precise arrangements and instrumentalities shown therein. In the drawings:

FIG. 1 includes images showing gametocytes of chloroquine resistant (PfDd2) clones that were untreated (left) and treated (right) with 88 nM of Compound I (Calxinin).

FIGS. 2A-2B provides graphs representing data relating to the parasitemia and survival of mice inoculated with *Plasmodium berghei* NK-65 infected red blood cells and subsequently untreated (control) or treated with Compound I (Calxinin). 10$^7$ *Plasmodium berghei* NK-65 (chloroquine-resistant) were administered by intraperitoneal injection into Swiss albino mice (6 mice/group). Infected mice were either treated with Calxinin or injected with DMSO alone (untreated control). Percent parasitemia was determined on days 3, 7 and 10-post infection (**=p<0.001; *=p<0.01) FIG. 2A The survival of the mice was followed up to day 30 post-infection using Kaplan-Meier survival analysis FIG. 2B Animal survivals were analyzed by a log rank test.

FIG. 3 provides graphs representing data relating to liver stage parasite growth and percent inhibition in HepG2 cells treated with Compound I (Calxinin). HepG2 cells were infected with *P. berghei* sporozoites and treated with Compound I (Calxinin) at the indicated concentration. After two days, the cells were fixed in Trizol, parasite load in the cells was determined by qPCR using parasite specific 18SrRNA primers, and % inhibition is plotted.

Figure 6A:
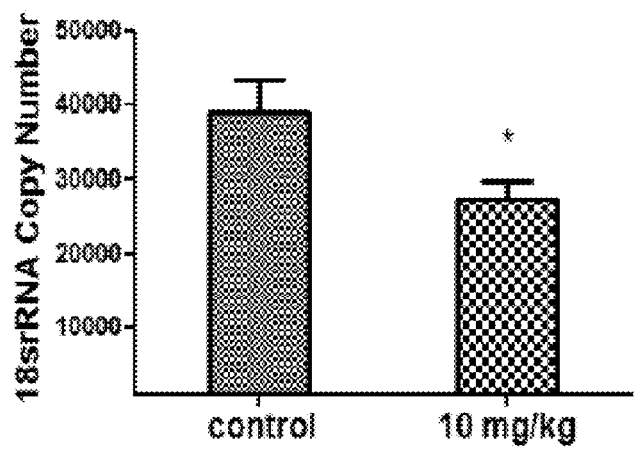
Figure 6B:
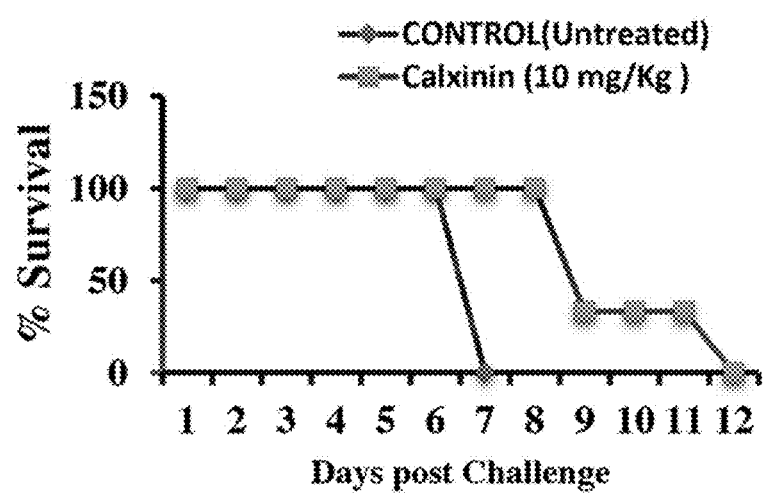

FIG. 6A is a graph showing the percent parasitemia in both treated with Compound I (Calxinin) or untreated (control) mice infected with *P. berghei*. FIG. 6B is a graph showing the percent survival in both treated with Compound I (Calxinin) or untreated (control) mice infected with *P. berghei*. On day 0, day 1 and day 2, mice were treated with Compound I (Calxinin) at 10 mg/kg (I.P). Livers of experimental mice were isolated 50 h post infection. RNAs were isolated from the homogenized sample followed by Real Time PCR by using parasite specific 18SrRNA primers.

FIGS. 7A-7D provide the results of ookinete inhibition and formation assays.

Figure 7A:
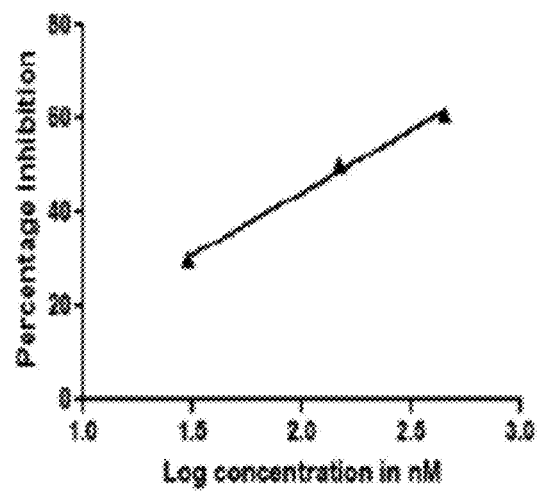
Figure 7B:
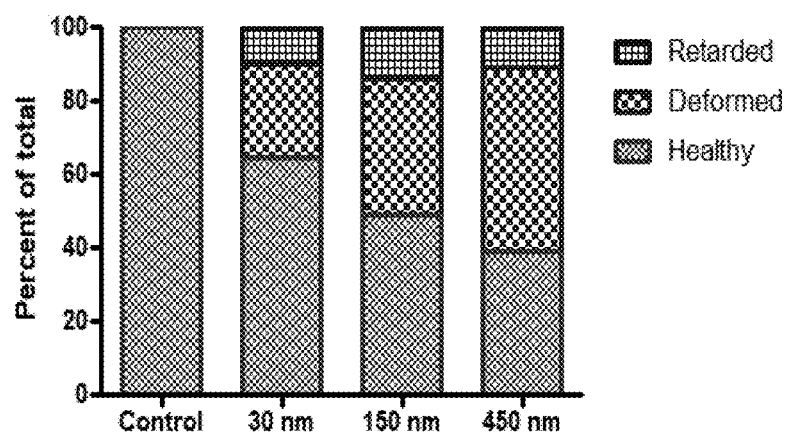
Figure 7C:
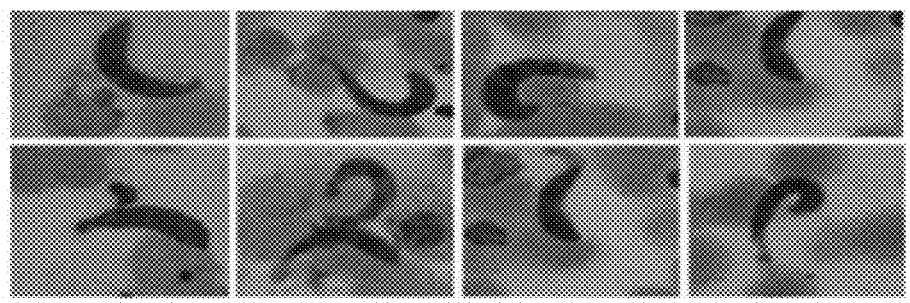
Figure 7D:
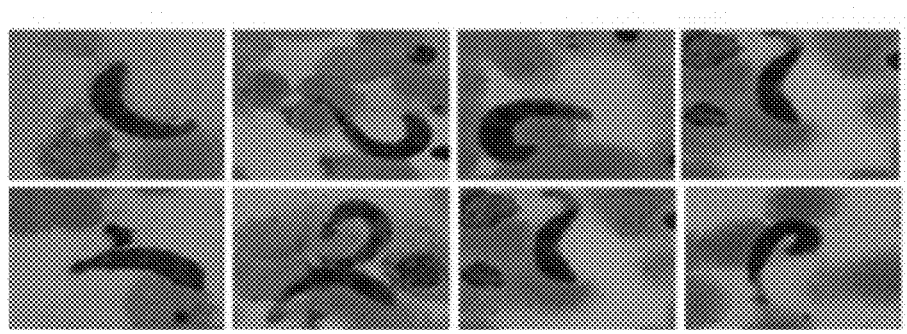
Figures 8A, 8B:
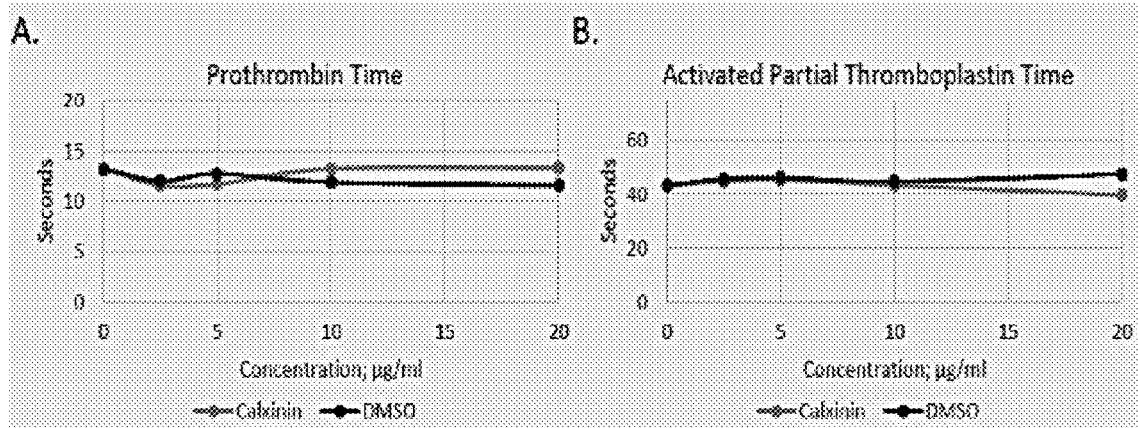
Figure 8C:
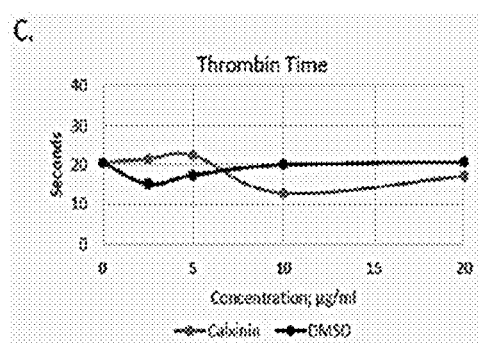
Figure 8D:
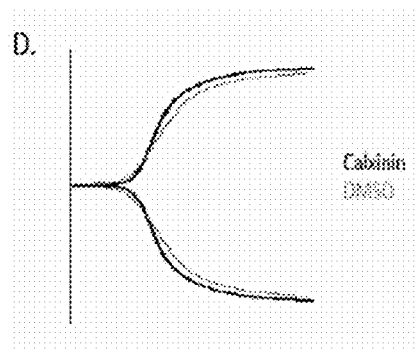
Figures 8E, 8F:
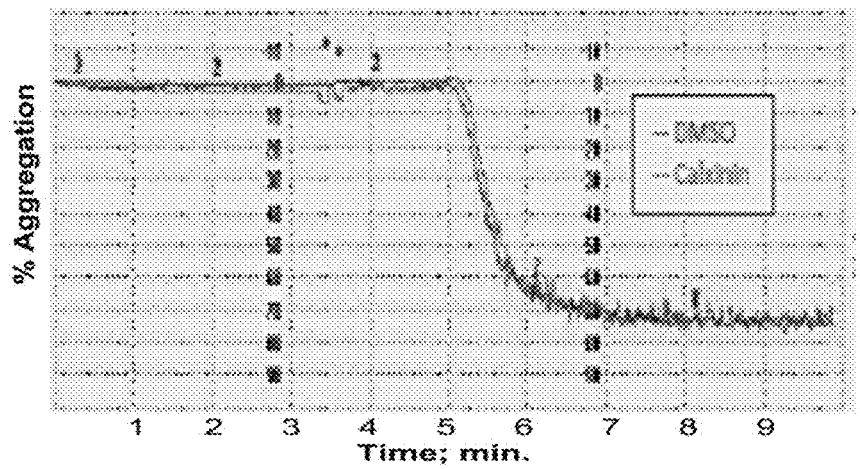

FIG. 7A provides a graph showing the percent ookinete inhibition in an in vitro assay against *P. berghei* GFPCON. FIG. 7B provides a bar graph showing the structural changes in ookinete formation observed when treated with Compound I (Calxinin) at the indicated concentrations. FIG. 7C provides representative images of the control (Healthy) Ookinete. Images were taken on NIKON 80i microscope at 100×. Smears were fixed with methanol and stained with Giemsa. FIG. 7D provides representative images of the deformed and retarded ookinete on treatment of Compound I (Calxinin) at 450 nanoMolar concentration. Images were taken on NIKON 80i microscope at 100×. Smears were fixed with methanol and stained with Giemsa.

FIGS. 8A-F show that there was no adverse impact of Compound I (Calxinin) on hemostatic parameters: (FIGS. 8A-8C) anticoagulant effect: (FIG. 8D) clot formation: and (FIG. 8E, FIG. 8F) agonist-induced aggregation of human platelets (20 µg/ml).

Figure 9:
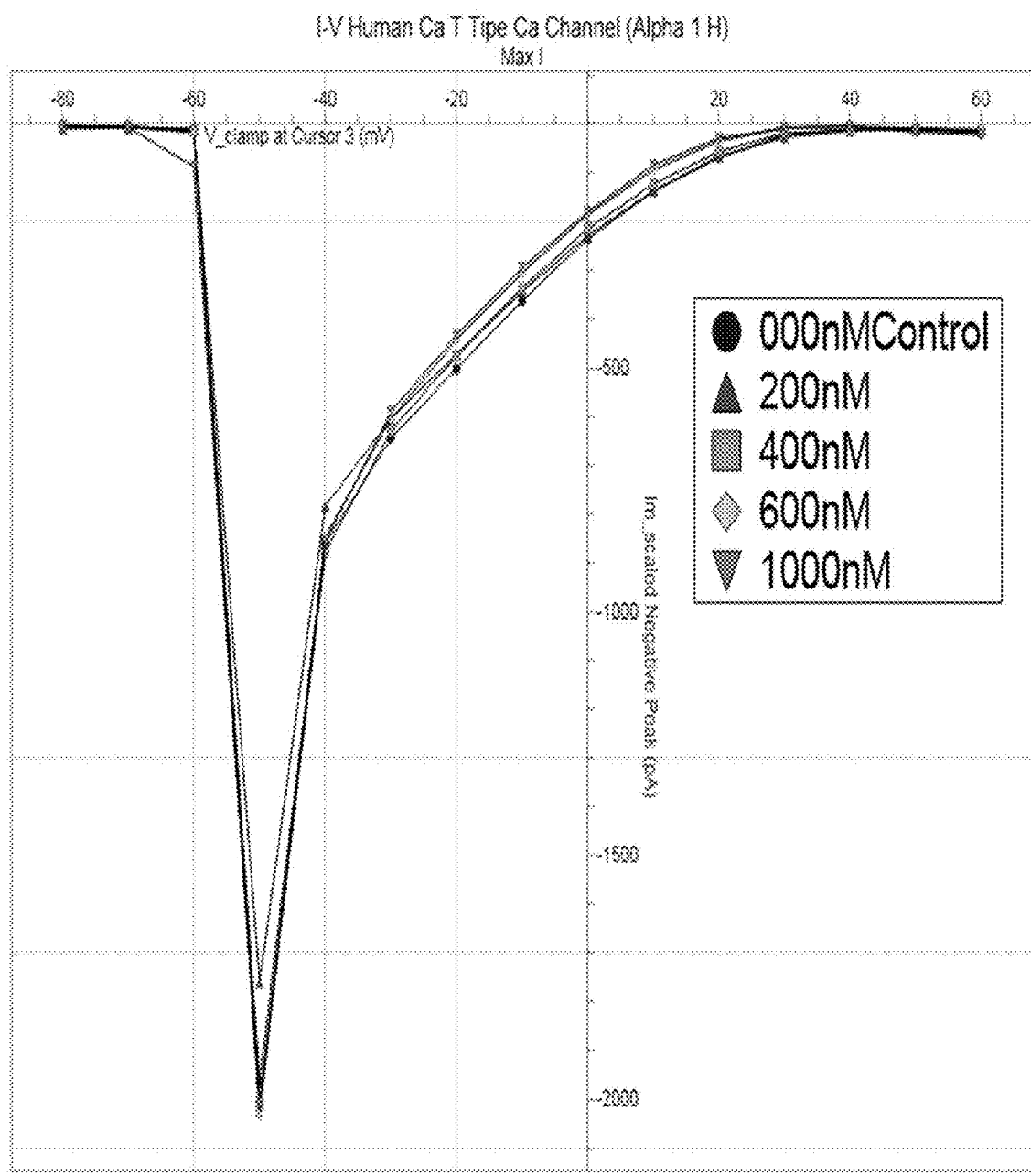

FIG. 9 depicts the data on Compound I (Calxinin) treated Human T-type calcium channel currents measured with the Patch clamp on the "whole cell" configuration in HEK 293 cells constitutively expressing human T type Calcium channel. No difference in the activity of the Calcium T Channel under DMSO treated and with increasing concentrations of the Calxinin was found. As shown, no difference in the amplitude of the calcium channel currents, nor in the dependence with the membrane potential of calcium channel activation even at 11 times the IC50 conc.

Figure 10:
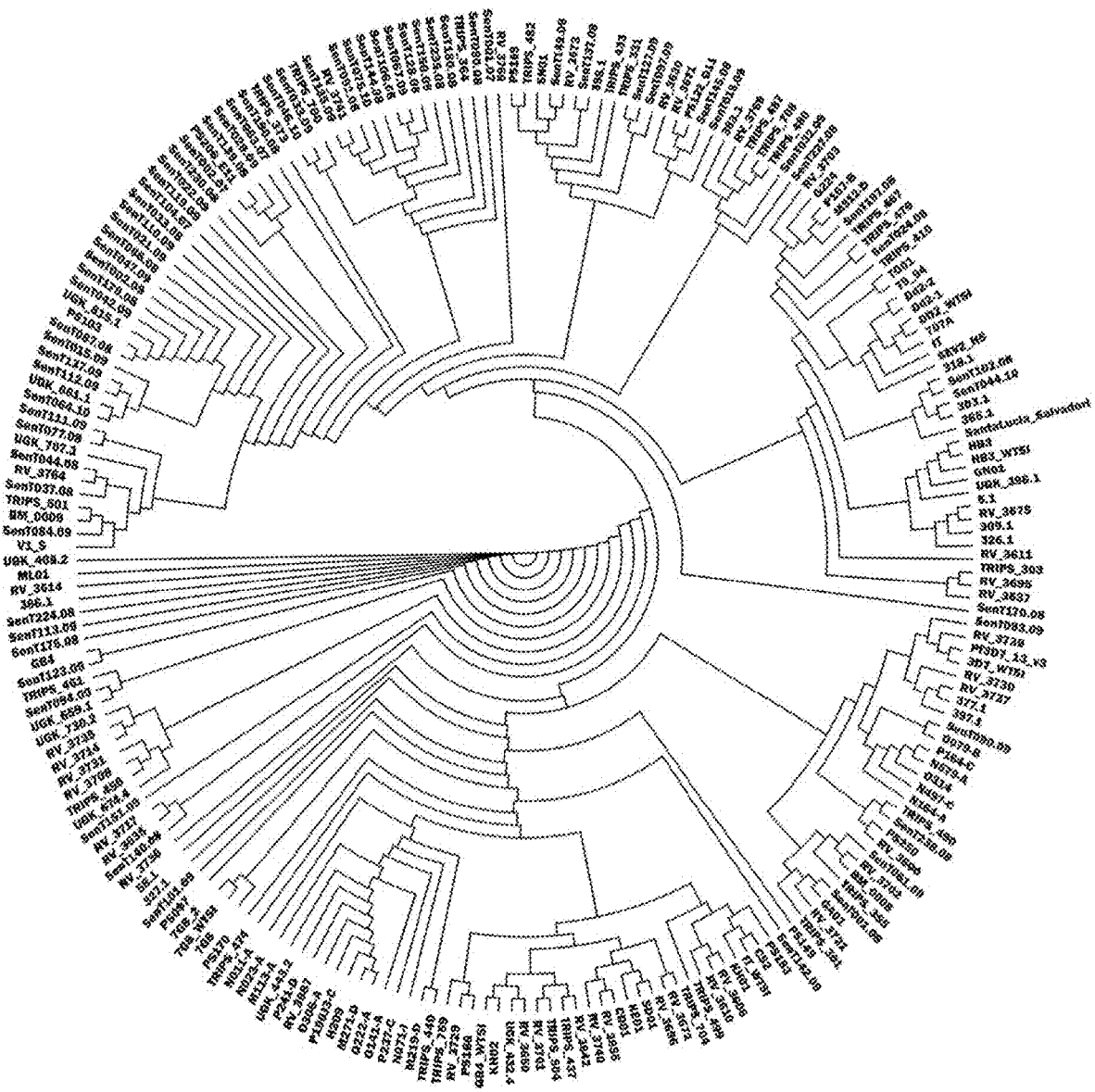

FIG. 10 depicts the phylogenetic tree of PF3D7_1313500 (SEQ ID NO: 1) sequence homologues generated using 218 field isolates around the world. All field isolates formed phylogenetic groups according to evolutionary niches due to geographical location or time of isolation. This shows high conservancy of the gene among these isolates.

Figure 11:
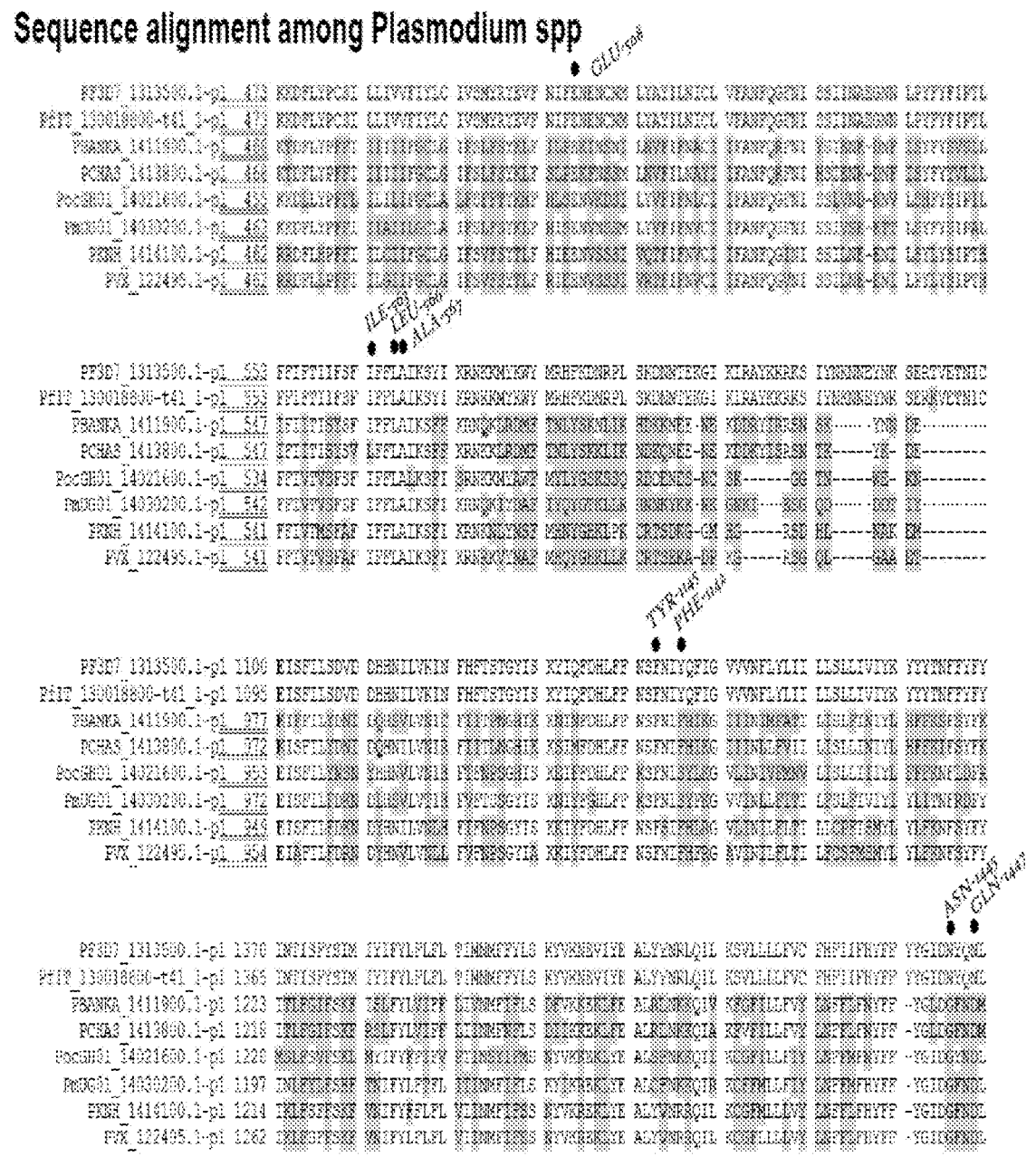

FIG. 11 provides multiple sequence alignment segments of PF3D7_1313500 (SEQ ID NO: 1) homologues from different *plasmodium* species. The binding pocket highlighted by a black pointer was highly conserved biochemically among all species highlighting its conservness even among distant species. This shows low chances of mutations and thus resistance due to biochemical hence functional importance. Any change changing the biochemical nature of the pocket will have a high fitness cost for the parasite.

Figure 12:
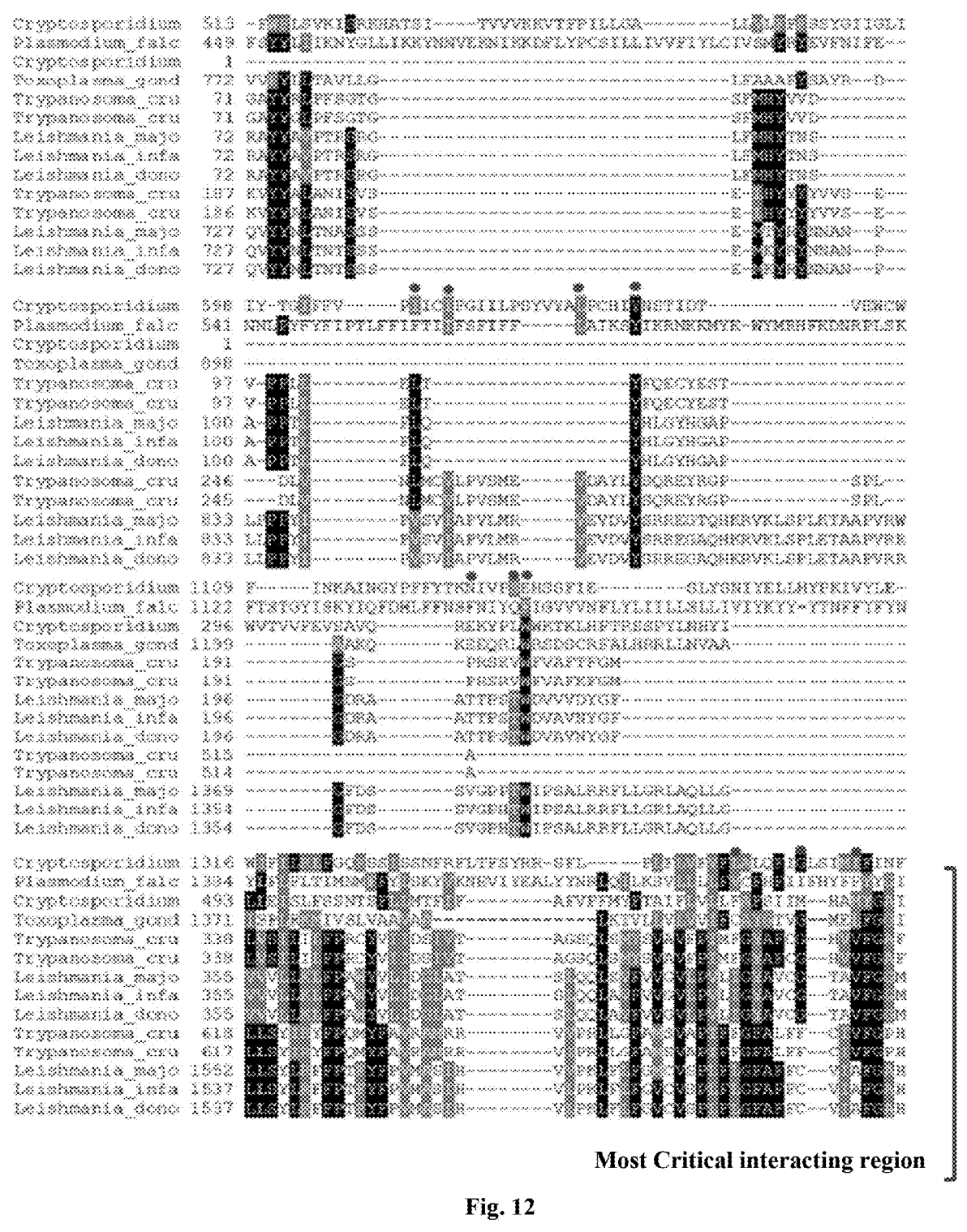

FIG. 12 provides multiple sequence alignment segments of PF3D7_1313500 (SEQ ID NO: 1) homologues from different intracellular parasitic protozoa. The binding pocket highlighted by a red dot was highly conserved biochemically among all species highlighting its conservness even among distant species. This shows high possibility of broad spectrum activity as already seen with two parasites from Apicoplexan and Kinetoplexan groups. Any change changing the biochemical nature of the pocket will have a high fitness cost for the parasite.

Figure 13:
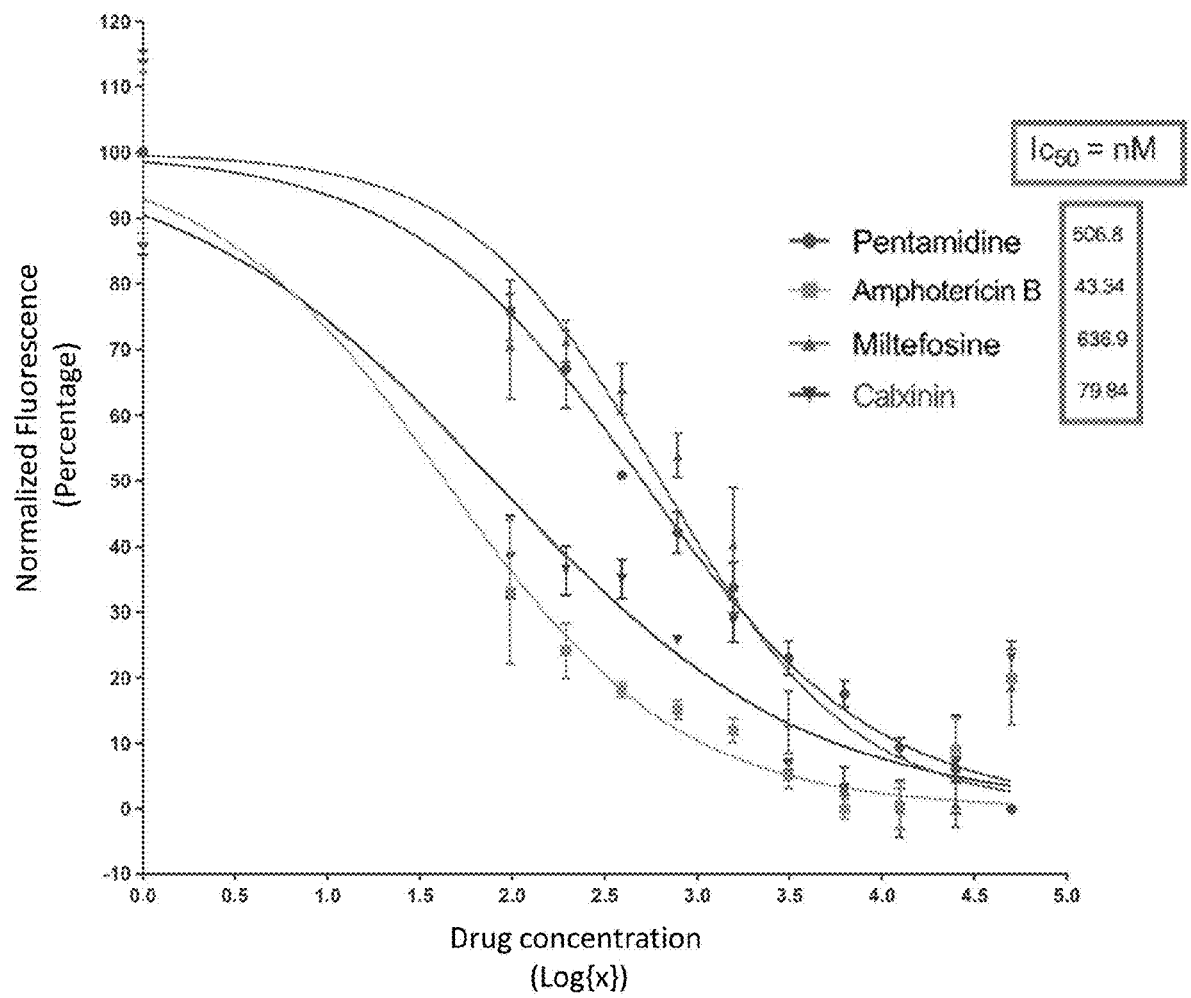

FIG. 13 is a graph showing the dose response curve of *Leishmania donovani* cultures treated with Pentamidine, Amphotericin B. Miltefosine and Calxinin (Compound I).

DETAILED DESCRIPTION OF INVENTION

In describing the invention, the following terminology will be used in accordance with the definitions set forth below. Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described herein. As used herein, each of the following terms has the meaning associated with it in this section. Specific and preferred values listed below for individual process parameters, substituents, and ranges are for illustration only; they do not exclude other defined values or other values falling within the preferred defined ranges.

As used herein, the singular forms "a", "an" and "the" include plural reference unless the context clearly dictates otherwise.

The terms "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

When the term "about" is used in describing a value or an endpoint of a range, the disclosure should be understood to include both the specific value and end-point referred to.

As used herein, the terms "comprising" "including," "having," "containing," "involving," and the like are to be understood to be open-ended, i.e. to mean including but not limited to.

Provided herein are compounds of Formula (I):

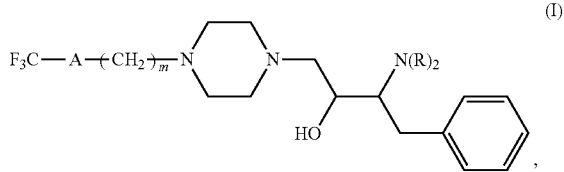

(I)

and pharmaceutically acceptable salts thereof, which are useful for treating protazoan parasitic diseases, such as malaria. For example, it has been found that Compound I (Calxinin):

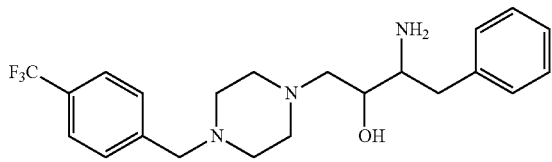 [SMILES: NC(Cc1ccccc1)C(O)CN1CCN(Cc2ccc(C(F)(F)F)cc2)CC1]

functions as a novel, potent, multi-stage antimalarial compound. The compounds disclosed herein can be prepared in a simple, cost-effective synthesis that is optimized for scalability. The compounds of the disclosure have been shown to block the parasite calcium channel, which is known to be critical for parasite survival. The compounds of the disclosure are effective at nanomolar concentrations against all stages of the malaria parasite life cycle (human), and exhibit a synergistic interaction with other anti-parasitic therapeutics, such as dihydroartemisinin ("DHA"). Further, the compounds disclosed herein do not exhibit cytotoxicity to human cell, and do not show any changes to blood parameters in mice. The compounds disclosed herein are effective in killing field isolates of malaria parasite, and have no indication of any toxicity at concentrations as high as 1200 mg/kg. Moreover, the compounds of the disclosure show favorable pharmacokinetics.

Compounds of Formula (I)

Provided herein are compounds that have a structure of Formula (I):

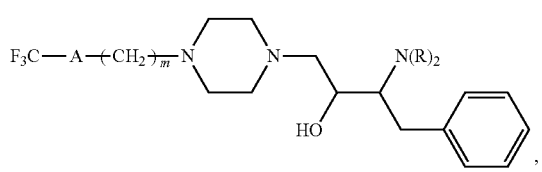

and pharmaceutically acceptable salts thereof, wherein A is $C_{6-10}$aryl; each R independently is H or $CH_3$; and m is 1, 2, or 3.

In some cases, A is $C_{6-10}$aryl. In some embodiments, A is phenyl or naphthyl. In various cases, A is phenyl. In various embodiments, $CF_3$-A is

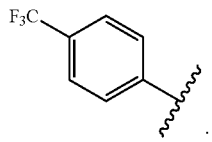

In some embodiments each R is H. In various embodiments, each R is $CH_3$. In some cases, one R is H and one R is $CH_3$. In various cases, m is 1. In some cases, m is 2. In various embodiments, m is 3. In some cases, $CF_3$-A is

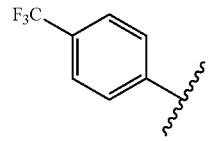 [SMILES: *c1ccc(C(F)(F)F)cc1]

and m is 1.

As used herein, the term "aryl" refers to an aromatic carbocycle, and can be monocyclic or polycyclic (e.g., fused bicyclic and fused tricyclic) carbocyclic aromatic ring systems. Examples of aryl groups include, but are not limited to, phenyl, naphthyl, tetrahydronaphthyl, phenanthrenyl, biphenylenyl, indanyl, indenyl, anthracenyl, fluorenyl, tetralinyl. Unless otherwise indicated, an aryl group can be an unsubstituted aryl group or a substituted aryl group.

A "substituted" functional group (e.g., a substituted alkyl, cycloalkyl, aryl, or heteroaryl) is a functional group having at least one hydrogen radical that is substituted with a non-hydrogen radical (i.e., a substituent). Examples of non-hydrogen radicals (or substituents) include, but are not limited to, alkyl, cycloalkyl, alkenyl, cycloalkenyl, alkynyl, ether, aryl, O-alkylene aryl, N-alkylene aryl, alkylene aryl, heteroaryl, heterocycloalkyl, hydroxy, hydroxyalkyl, haloalkoxy, amido, oxy (or oxo), alkoxy, ester, thioester, acyl, carboxyl, cyano, nitro, amino, sulfhydryl, and halo (e.g., fluoro, chloro, bromo, or iodo). When a substituted alkyl group includes more than one non-hydrogen radical, the substituents can be bound to the same carbon or two or more different carbon atoms.

In some embodiments, the compound of Formula (I) has a structure of Compound I (Calxinin):

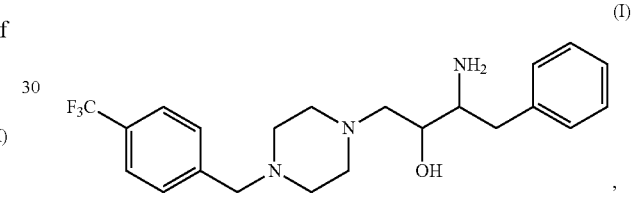

or a pharmaceutically acceptable salt thereof. In some cases, the compound of Formula (I) or pharmaceutically acceptable salt thereof exhibits stereochemistry, as shown in Compound Ia:

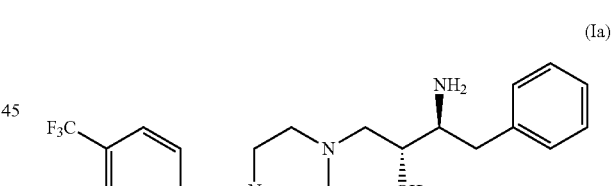

It has been found that compounds having the specific selection of substituents of Formula (I) bind to the parasitic calcium channel, allowing them to exhibit multi-stage anti-parasitic activity and act as potent therapeutics for treating protozoan parasitic diseases.

The compounds of the disclosure have a piperazine linker flanked by a trifluoromethyl-substituted ring and a hydroxyethylamine moiety attached to a benzyl group. The piperazine linker provides rigidity to the middle portion of the structure, keeping both rings of the compound stretched out for interacting with the binding site. The piperazine ring was found to bind amphiphatically to a mixed pocket with Val671 and TYR672. Such amphipathic pores in ion channels and transporters concentrate an effective ionic cloud-like accumulation, facilitating transport through the pore. The trifluoromethyl moiety on ring A has direct interactions with the calcium binding channel at ASN675 and TYR 963, allowing the compounds of the disclosure to have good binding affinity with the calcium channels in a parasite. The trifluoromethyl group is useful for targeting the molecule to the active site, and provides molecular flexibility, increasing binding affinity, and balanced lipophilicity. The hydroxyl group of the hydroxyethylamine binds to GLN1265 of the target. The benzyl ring that is attached to the hydroxyethylamine has the appropriate hydrophobicity to bind to a hydrophobic pocket near the channel core, anchoring the molecule in place, without causing toxicity.

Synthesis of Compounds of Formula (I)

The compounds described herein can be synthesized by any method known in the art. For example, the compounds can be prepared as shown in Scheme 1, below.

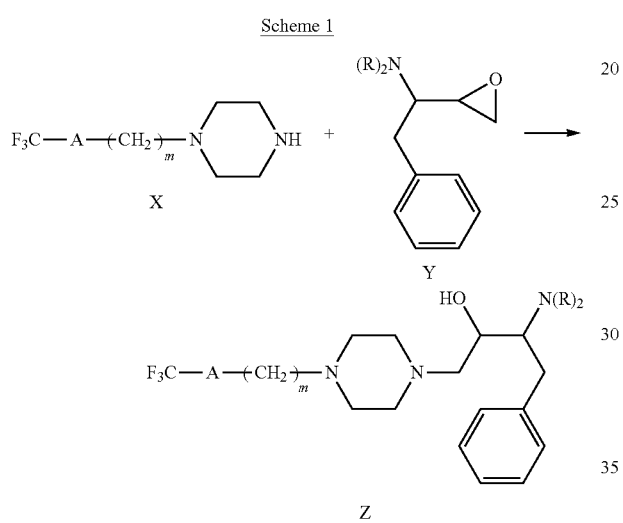

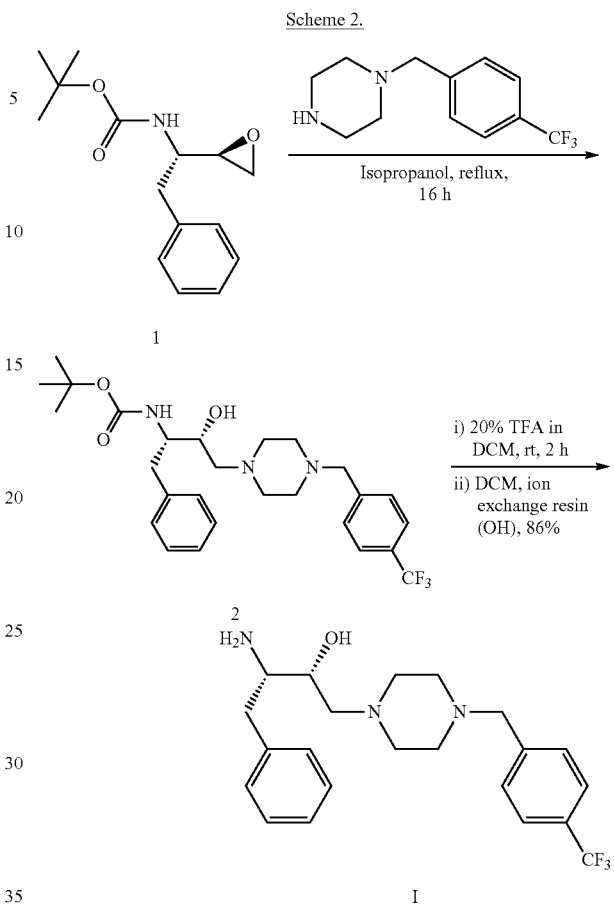

As shown in Scheme 1, compound Z can be accessed via a nucleophilic epoxide ring opening reaction from reactants X and Y, wherein the variables are as described herein. In some embodiments, the amino group of compound Y is protected before the ring opening reaction. Amino protecting groups are well known to those skilled in the art. Thus, the protecting group can be any suitable amino protecting group known to those skilled in the art, such as a tert-butoxycarbonyl ("BOC") protecting group. In embodiments, X and Y are dissolved in an organic solvent having a boiling point of 50° C. or more, such as isopropanol, and refluxed for an appropriate period of time, such as 8-20 hours, or 16 hours. In embodiments wherein the amino group is protected, the protecting group can be removed after the nucleophilic epoxide ring opening ring by methods well-known to those skilled in the art. For example a BOC protecting group can be removed using trifluoroacetic acid (TFA).

In some embodiments, provided is a method according to Scheme 2 that includes adding 1-(4-(trifluoromethyl)benzyl) piperazine to a solution of BOC-protected epoxide (1) in 2-propanol to form a mixture, refluxing the mixture for a time period sufficient to form a reaction mixture, concentrating the reaction mixture to yield an intermediate compound (2), dissolving the intermediate compound in a solution that includes trifluoroacetic acid to yield a product comprising a hydroxyethylamine-based piperazine analog (I).

In particular, 1-(4-(trifluoromethyl)benzyl)piperazine (e.g., 0.46 mol) may be added to a solution of BOC-protected epoxide (e.g., 0.38 mol; (identified in Scheme 2 with reference number 1)) in 2-propanol and the mixture can be refluxed, for example, for sixteen hours. The resulting reaction mixture may be concentrated under reduced pressure to afford an intermediate compound (identified in Scheme 2 with reference number 2) as a white solid. The intermediate compound (2) can then be dissolved in 20% trifluoroacetic acid (TFA) with dichloromethane (DCM), which affords the desired hydroxyethylamine-based piperazine compound (i.e., Compound I (Calxinin) in Scheme 2). Thereafter. TFA salt may be eliminated with a TFA scavenger using basic anion exchange resin (e.g., Amberlite™ IRA-402) which can be added until the mixture becomes basic in nature to give a white solid, which may be further purified by column chromatography using a neutral alumina such that the compound is isolated (e.g., 1% M:C).

Pharmaceutical Formulations

Also provided herein are pharmaceutical formulations that include the compounds of the disclosure, and one or more pharmaceutically acceptable excipients. As used herein, the term "excipient" means any pharmaceutically acceptable additive, carrier, diluent, adjuvant, or other ingredient, other than the active pharmaceutical ingredient (API). As used herein, the term "pharmaceutically acceptable" means that the referenced substance, such as a compound of the present disclosure, a salt of the compound, a formulation containing the compound, or a particular excipient, is safe and suitable for administration to a subject or patient.

The compounds disclosed herein can be as a pharmaceutically acceptable salt. As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al. describe pharmaceutically acceptable salts in detail in *J. Pharmaceutical Sciences*, 1977, 66, 1-19, which is incorporated herein by reference. Pharmaceutically acceptable salts of the compounds of this disclosure include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, trifluoroacetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, glutamate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts of compounds containing a carboxylic acid or other acidic functional group can be prepared by reacting with a suitable base. Such salts include, but are not limited to, alkali metal, alkaline earth metal, aluminum salts, ammonium, $N^*(C_{1-4}alkyl)_4$ salts, and salts of organic bases such as trimethylamine, triethylamine, morpholine, pyridine, piperidine, picoline, dicyclohexylamine. N,N'-dibenzylethylenediamine, 2-hydroxyethylamine, bis-(2-hydroxyethyl)amine, tri-(2-hydroxyethyl)amine, procaine, dibenzylpiperidine, dehydroabietylamine, N,N'-bisdehydroabietylamine, glucamine. N-methylglucamine, collidine, quinine, quinoline, and basic amino acids such as lysine and arginine. This invention also envisions the quaternization of any basic nitrogen-containing groups of the compounds disclosed herein. Water or oil-soluble or dispersible products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

The compounds of the disclosure can be administered to a subject or patient in a therapeutically effective amount. As used herein, the term "therapeutically effective amount" means an amount of a compound or combination of therapeutically active compounds described herein that ameliorates, attenuates or eliminates one or more symptoms of a particular disease or disorder (e.g., macular edema), or prevents or delays the onset of one of more symptoms of a particular disease or disorder. As used herein, the terms "patient" and "subject" may be used interchangeably and mean animals, such as dogs, cats, cows, horses, and sheep (i.e., non-human animals) and humans. Particular patients are mammals (e.g., humans). The term patient includes males and females. The compounds can be administered alone or as part of a pharmaceutically acceptable composition or formulation. In addition, the compounds can be administered all at once, as for example, by a bolus injection, multiple times, e.g. by a series of tablets, or delivered substantially uniformly over a period of time, as for example, using transdermal delivery. It is also noted that the dose of the compound can be varied over time.

The compounds disclosed herein and other pharmaceutically active compounds, if desired, can be administered to a subject or patient by any suitable route, e.g. orally, rectally, parenterally, (for example, intravenously, intramuscularly, or subcutaneously) intracisternally, intravaginally, intraperitoneally, intravesically, or as a buccal, inhalation, or nasal spray. The administration can be to provide a systemic effect (e.g. eneteral or parenteral). All methods that can be used by those skilled in the art to administer a pharmaceutically active agent are contemplated.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Microorganism contamination can be prevented by adding various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents delaying absorption, for example, aluminum monostearate and gelatin.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, and silicic acid: (b) binders, as for example, carboxymethylcellulose, alginates, gelatin, polyvinylpyrrolidone, sucrose, and acacia: (c) humectants, as for example, glycerol; (d) disintegrating agents, as for example, agar-agar, calcium carbonate, potato or tapioca starch, alginic acid, certain complex silicates, and sodium carbonate: (a) solution retarders, as for example, paraffin: (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, and tablets, the dosage forms may also comprise buffering agents. Solid compositions of a similar type may also be used as fillers in soft and hard filled gelatin capsules using such excipients as lactose or milk sugar, as well as high molecular weight polyethylene glycols, and the like.

Solid dosage forms such as tablets, dragees, capsules, pills, and granules can be prepared with coatings and shells, such as enteric coatings and others well known in the art. The solid dosage forms may also contain opacifying agents. Further, the solid dosage forms may be embedding compositions, such that they release the active compound or compounds in a certain part of the intestinal tract in a delayed manner. Examples of embedding compositions that can be used are polymeric substances and waxes. The active compound can also be in micro-encapsulated form, optionally with one or more excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

Besides such inert diluents, the composition can also include adjuvants, such as wetting agents, emulsifying and suspending agents, sweetening, flavoring, and perfuming agents. Suspensions, in addition to the active compound, may contain suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal administration are preferably suppositories, which can be prepared by mixing the compounds of the disclosure with suitable non-irritating excipients or carriers such as cocoa butter, polyethylene glycol or a suppository wax, which are solid at ordinary room temperature, but liquid at body temperature, and therefore, melt in the rectum or vaginal cavity and release the active component.

The compounds of the disclosure can be administered to a subject or patient at dosage levels in the range of about 0.1 to about 3,000 mg per day. For a normal adult human having a body weight of about 70 kg, a dosage in the range of about 0.01 to about 100 mg per kilogram body weight is typically sufficient. The specific dosage and dosage range that will be used can potentially depend on a number of factors, including the requirements of the subject or patient, the severity of the condition or disease being treated, and the pharmacological activity of the compound being administered. The determination of dosage ranges and optimal dosages for a particular subject or patient is within the ordinary skill in the art.

Optionally, the compounds of the disclosure (compounds of Formula (I), Compound I, Compound Ia), and pharmaceutically acceptable salts thereof can be administered with one or more additional therapeutic agents. Similarly, in various embodiments of the disclosure, the method comprises administering one or more additional therapeutic agents simultaneously with the compound of the disclosure or pharmaceutically acceptable salt thereof. In various embodiments, the method comprises administering one or more additional therapeutic agents and the compound of the disclosure or pharmaceutically acceptable salt sequentially.

In some embodiments, the additional therapeutic can be present in the same composition as the compound of the disclosure or pharmaceutically acceptable salt thereof. In some cases, the additional therapeutic can be present in a separate composition as the one comprising the compound of the disclosure or pharmaceutically acceptable salt thereof. In some embodiments, the additional therapeutic agent is another anti-parasitic therapeutic. In various embodiments, the other anti-parasitic therapeutic is one that is currently in use to treat parasitic diseases. Contemplated anti-parasitic therapeutics that can be administered with the compounds of the disclosure (compounds of Formula (I), Compound I, and Compound Ia) and pharmaceutically acceptable salts thereof include quinine, chloroquine ("CQ"), proguanil, sulfadoxine-pyrimethamine, mefloquine, atovaguone, doxycycline ("DOX"), clindamycin, artemisinin, and dihydroartemisinin ("DHA"). In some cases, the compound of the disclosure or pharmaceutically acceptable salt thereof is administered in combination with DHA. In various embodiments, Compound I is administered in combination with DHA. In various cases, Compound Ia is administered in combination with DHA. Advantageously, combinations of the compounds of the disclosure (compounds of Formula (I), Compound I, and Compound Ia) and pharmaceutically acceptable salts thereof show a synergistic effect against in vitro growth of the P/Dd2 (chloroquine resistant) strain.

Methods

Effective malaria control is severely impeded by therapeutics rendered ineffective due to resistance parasite, prohibitive costs, and cumulative toxic effects. Multi-stage antimalarial compounds of Formula (I), such as Compound I and Compound Ia and pharmaceutically acceptable salts of the foregoing, with novel mechanisms of action have been developed to broaden the therapeutic scope and overcome resistance to frontline therapeutics. The compounds described herein also have been found to show favorable pharmacokinetics.

It has been found that the compounds of the disclosure (compounds of Formula (I), Compound I. Compound Ia), and pharmaceutically acceptable salts thereof target and/or bind to an uncharacterized 'voltage gated calcium channel protein' comprising the amino acid sequence set forth in SEQ ID NO: 1. In some embodiments, the compounds of the disclosure (compounds of Formula (I), Compound I. Compound Ia), and pharmaceutically acceptable salts thereof target and/or bind to an uncharacterized voltage gated calcium channel consisting of the amino acid sequence set forth in SEQ ID NO: 1 It has further been found that calcium sensing/binding region (i.e., functional portion) of the calcium channel protein comprises amino acids [Name, Position] GLU (508); ILE (563); LEU (566); ALA (567); PHE (1142); TYR (1145); ASN (1445): GLN (1447) of SEQ ID NO: 1 (also set forth in SEQ ID NO: 2). In some cases, the core region of the calcium channel protein consists of the amino acid sequence set forth in SEQ ID NO: 2. Thus, in some cases, the compounds of the disclosure (compounds of Formula (I), Compound I, Compound Ia), and pharmaceutically acceptable salts thereof, target and/or bind to the core region of the calcium channel protein comprising the amino acid sequence set forth in SEQ ID NO: 2.

In various cases, the compounds of the disclosure (compounds of Formula (I), Compound 1, Compound Ia), and pharmaceutically acceptable salts thereof, target and/or bind to the core region of the calcium channel protein consisting of the amino acid sequence set forth in SEQ ID NO: 2.

Through an in-silico pipeline followed by in-vitro and in-vivo validations and characterizations, an uncharacterized parasite protein (PlasmoDB ID: PF3D7_0212500) was found to be a potential target of the compounds of the disclosure, such as compounds of Formula (I), Compound I, Compound Ia (Calxinin), and pharmaceutically acceptable salts of the foregoing. The gene codes for a putative calcium modulator, highly conserved among plasmodia and essential according to piggyBac insertion mutagenesis. Data shows that Compound I (Calxinin) has significant inhibitory activity against asexual stages with $IC_{50}$s of 90 nM (±1.9) in drug sensitive (CQ-sensitive) {3D7} and 88 nM (±1.1) in drug resistant (CQ-resistant) {DD2} parasites. Activity against sexual stage I and II gametocytes with Calxinin ($IC_{50}$, 88 nM) showed decreased proportion of stage III to V gametocytes (up to 59%) and distorted cellular morphology. Further, interactions between the Calxinin-DHA showed synergistic effect in PfDd2 strain. Cell cytotoxicity assays in primary and human cells showed no toxicity up to 30 μM, a several 100-fold higher concentration than required for parasite killing. The screening against freshly collected field isolates of *P. falciparum* infected blood showed $IC_{50}$ values of 643.3 nM (±177. 2), which is lower than lab strain, and no spontaneous resistance. Further testing on artemisinin ("ART") resistant strain also showed inhibitory properties identical to field and lkab strain. A single dose (10 mg/kg) of Calxinin in CQ-resistant rodent strain of *P. berghei* NK64 showed significant activity against mixed blood stage parasites accompanied by a 30% reduction in parasite load. Additionally, in-vitro liver stage testing showed $IC_{50}$ of 65 nM and in-vitro ookinete inhibition $IC_{50}$ was 150 nM. Thus, the compounds of the disclosure (e.g., compounds of Formula (I), Compound I, Compound Ia), and pharmaceutically acceptable salts of the foregoing, function as nontoxic, calcium transporter modulators with therapeutic, prophylactic and transmission blocking potential against resistant parasite to current antiparasitic compounds, such as antimalarials. See the Examples section and the Figures for further information.

The activity of Compound I (Calxinin) also was tested against *Leishmania*. The Calxinin treatment of Amastigotes of *L. donavani* showed significant inhibition of parasites inside the THP-1 macrophages. Results interestingly showed Calxinin is more potent ($IC_{50}$ 79.84 nM) than the currently used drugs (Miltefosine and Pentamidine) and similar to that of Amphotericin B, which is known to be highly toxic to the host. See the Examples section for further details.

Furthermore, the prevalence of inherent mutation and/or random genetic variation in the gene(s) encoding for Calxinin target gene 'voltage gated calcium channel' was addressed by data mining of the gene sequence encoding this protein from 218 isolates across the endemic regions including areas where current Chloroquine/Artemisinin resistance is widespread was performed. All field isolates formed phylogenetic groups according to evolutionary niches due to geographical location or time of isolation, showing high conservancy of the gene among these isolates. Low variation was found in any of the isolates sequenced, and the Calxinin key interacting residues were 100% conserved in all the 218 isolates, indicating the essentiality of this protein for parasite survival and functional importance of Calxinin binding domain (FIG. 10).

It also has been found that the voltage gated calcium channel in the parasites that cause malaria, Leishmaniasis. Toxoplasmosis, Chagas, and Cryptosporidiosis are highly conserved, having less than 6% homology to any human channel/transporter (FIG. 11 and FIG. 12). Thus, the data provided for the parasites that cause malaria and Leishmaniasis can be extrapolated to Toxoplasmosis, Chagas, and Cryptosporidiosis.

Accordingly, provided herein is a method of treating a protozoan parasitic disease in a subject comprising administering to the subject a therapeutically effective amount of a compound of the disclosure (compound of Formula (I), Compound I, Compound Ia), or a pharmaceutically acceptable salt thereof. In some embodiments, the protozoan parasitic disease is malaria, Leishmaniasis, Toxoplasmosis, Chagas, or Cryptosporidiosis. In some cases, the protozoan parasitic disease is malaria. In some embodiments, the malaria is liver stage malaria. In various cases, the malaria is blood stage malaria. In some embodiments, the malaria is transmission (gametocyte and/or ookinete) stage malaria. In some embodiments, the subject is infected with a malaria-causing parasite. In various embodiments, the malaria-causing parasite is *Plasmodium falciparum, Plasmodium vivax, Plasmodium ovale curtisi, Plasmodium knowlesi, Plasmodium berghei*, or *Plasmodium malariae*. In some embodiments, the malaria-causing parasite is *Plasmodium falciparum*. In some cases, the *Plasmodium falciparum* or *Plasmodium berghei* parasite is resistant to chloroquine ("CQ"), artemisinin ("ART"), dihydroartemisinin ("DHA"), or combinations thereof. In some embodiments, the protozoan parasitic disease is Leishmaniasis. In various embodiments, the subject is infected with a Leishmaniasis-causing parasite. In some cases, the Leishmaniasis-causing parasite is *Leishmania donovani, Leishmamaa major, Leishmania tropica, Leishmania* braziliensts. *Leishmania mexicana. Leishmania amazonensis*, or *Leishmania Chagasi*. In various cases, the Leishmaniasis-causing parasite is *Leishmania donovani, Leishmania major*, or *Leishmania Mexicana*. In various cases, the Leishmaniasis-causing parasite is *Leishmania donovani*. In various cases, the protozoan parasitic disease is Toxoplasmosis. In some embodiments, the subject is infected with a Toxoplasmosis-causing parasite. In various cases, the Toxoplasmosis-causing parasite is *Toxoplasma gondii*. In some embodiments, the protozoan parasitic disease is Chagas. In various cases, the subject is infected with a Chagas-causing parasite. In some embodiments, the Chagas-causing parasite is Typanosoma *cruzi*. In various embodiments, the protozoan parasitic disease is Cryptosporidiosis. In some cases, the subject is infected with a Cryptosporidiosis-causing parasite. In various cases, the Cryptosporidiosis-causing parasite is *Cryptosporidium parvum* and *Cryptosporidium hominis*. In some embodiments, the Trypanosomiasis presents in the form of African sleeping sickness.

As used herein, the terms "treat," "treating," "treatment," and the like refer to eliminating, reducing, or ameliorating a disease or condition, and/or symptoms associated therewith. Although not precluded, treating a disease or condition does not require that the disease, condition, or symptoms associated therewith be completely eliminated. As used herein, the terms "treat," "treating," "treatment," and the like may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition. The term "treat" and synonyms contemplate administering a therapeutically effective amount of a compound of the disclosure to an individual in need of such treatment. Within the meaning of the disclosure, "treatment" also includes relapse prophylaxis or phase prophylaxis, as well as the treatment of acute or chronic signs, symptoms and/or malfunctions. The treatment can be orientated symptomatically, for example, to suppress symptoms.

It can be effected over a short period, be oriented over a medium term, or can be a long-term treatment, for example within the context of a maintenance therapy. As used herein, the terms "prevent," "preventing," "prevention," are art-recognized, and when used in relation to a condition, such as a protozoan parasitic disease, is well understood in the art, and includes administration of a composition which reduces the frequency of, or delays the onset of, symptoms of a medical condition in a subject relative to a subject which does not receive the composition. Thus, prevention of malaria includes, for example, reducing the symptoms associated with malaria, such as fever, shaking, chills, headache, muscle ache, tiredness, diarrhea, anemia, and/or jaundice in a treated population versus an untreated control population, e.g., by a statistically and/or clinically significant amount.

In jurisdictions that forbid the patenting of methods that are practiced on the human body, the meaning of "administering" of a composition to a human subject or patient shall be restricted to prescribing a controlled substance that a human subject or patient will self-administer by any technique (e.g., orally, inhalation, topical application, injection, insertion, etc.). The broadest reasonable interpretation that is consistent with laws or regulations defining patentable subject matter is intended. In jurisdictions that do not forbid the patenting of methods that are practiced on the human body, the "administering" of compositions includes both methods practiced on the human body and also the foregoing activities.

Uses of the compounds disclosed herein in the preparation of a medicament for treating the diseases and disorders described herein are provided.

EXAMPLES

Synthesis of Compound I (Calxinin):

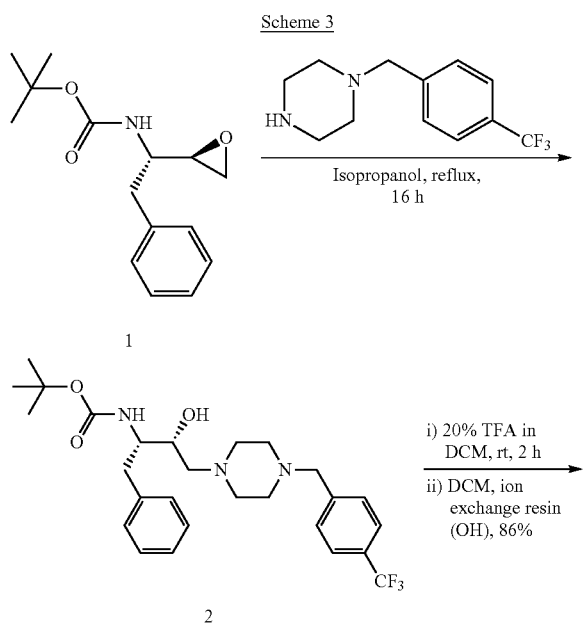

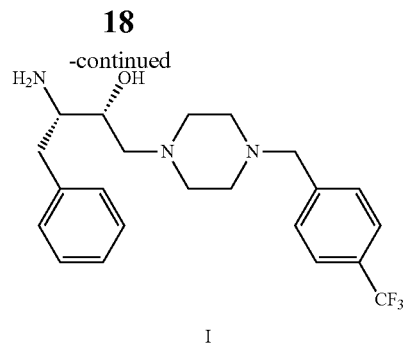

Firstly, the commercially available epoxide, (2R, 3S)-3-(N-BOC-amino)-1-oxirane-4-phenylbutane 1 (0.38 mol) was dissolved in isopropanol (15 mL), 1-(4-(trifluoromethyl)benzyl)piperazine (0.46 mol) was added, and the contents were refluxed for 16 hours. The resulting reaction mixture was concentrated under reduced pressure to afford intermediate compound 2, which was used for further reactions without purification. Compound 2 was dissolved in 20% trifluoroacetic acid (TFA) with dichloromethane (DCM), which generated a TFA salt in situ. The TFA salt was treated with TFA scavenger using basic anion exchange resin (Amberlite IRA-402) to result in Compound I (Calxinin). The crude product was further purified by column chromatography in neutral alumina gel (1% methanol:chloroform) to isolate Compound I (Calxinin) in 86% yield. The retardation factor (Rf) was 0.23 in 5% methanol/chloroform. MP. 93-95° C. $^1$H NMR (400 MHz, CDCl$_3$): δ 7.55 (d, J=7.4 Hz, 2H), 7.43 (d, J=7.4 Hz, 2H), 7.28 (t, J=6.8 Hz, 2H), 7.20 (s, 2H), 7.19 (s, 1H), 3.60 (d, J=7.9 Hz, 1H), 3.53 (s, 2H), 2.92-2.83 (m, J=17.1, 6.5 Hz, 2H), 2.66 (d, J=7.4 Hz, 2H), 2.64-2.56 (m, 3H), 2.45 (s, 6H), 2.40-2.33 (m, J=12.3, 2.6 Hz, 1H). $^{13}$C NMR (100 MHz, CDCl$_3$): δ 142.55, 139.20, 129.59, 129.38, 129.27, 128.61, 126.41, 125.69, 125.26, 125.23, 122.99, 68.80, 62.45, 61.20, 55.41, 53.27, 41.47.

Liver stage infection in HepG2 cells: Salivary glands of *Anopheles stephensi* mosquitoes infected with green fluorescent protein (GFP)-expressing *P. berghei* ANKA (Insectary at National Institute of Immunology, New Delhi, India) were dissected out. Sporozoites were perched in complete medium (Dulbecco's Modified Eagle Medium (DMEM)) with 10% fetal bovine serum (FBS), 3% penicillin-streptomycin (P/S)), and allowed to infect HepG2 cells. The cells were already treated with Calxinin at various concentrations (0.1 µM, 1 µM and 10 µM). The plate was centrifuged at 3000 rpm for 5 minutes to ensure the sporozoites settled down in the plate, and then placed in the incubation at 37° C. for 3 hours. Afterwards, media was replaced with pre-warmed medium (DMEM, 10% FBS, 3% P/S, and 0.1% Fungizone) supplemented with dimethyl sulfoxide (DMSO), and Calxinin at indicated concentrations. After two days, the cells were treated with Trizol and freeze-dried at −80° C. RNA isolation followed by reverse transcription polymerase chain reaction (RTPCR) was done to estimate the parasite load in the infected cells.

[1] Liver-stage infection in mice, treatment and survival assay: GFP-expressing *P. berghei* ANKA were grown in *Anopheles stephensi* mosquitoes in the insectary at National Institute of Immunology (New Delhi, India). Sporozoite count per salivary gland and infectivity was determined before the experimental infection of mice by the mosquito bites. Briefly, anaesthetized mice were exposed to a cage of sporozoite carrying starved mosquitoes (100 mosquito/5 mouse) for 15 minutes with intermittent disturbing of mosquito every 2-3 minute in order to encourage biting and injection of more sporozoite. Biting was done at 22+1° C. and dark condition maintained in an incubator. First dose (10 mg/Kg) was given 24 hours before the infection, second dose was given two hours post sporozoite challenge (biting) drug was given intraperitoneally (I.P.). Remaining dosages were given 24 h post challenge.

[2] For calculating parasite load, liver of experimental mice were isolated 50 h post infection. Mice were anesthetized, abdominal area sterilized with 70% ethanol and liver dissected out. Liver was homogenized in precold denaturating solution. RNAs were isolated from the homogenized sample followed by Real Time polymerase chain reaction (PCR).

[3] In vitro Ookinete inhibition assay of Calxinin. To determine whether Compound I (Calxinin) is blocking the growth of the transmission stage of malaria GFP-expressing P. berghei ANKA constitutively (Pb-GFPcon), which expresses the GFP during all the developmental stages, was used during in vitro experiments. Compound I (Calxinin) was tested in nanomolar range for its ability to inhibit ookinete development. Early gametocyte stage was maintained in vitro by incubating in ookinete media containing Xanthrunic acid and various other nutrients (complete DMEM) and pH 8.0. For the inhibition assay, culture plates containing Calxinin at different concentrations were incubated for about 24 h at 19° C. on a shaker and in the dark. After 24 h, ookinete development was checked by generating blood smears from the cultures. Smears were fixed, stained with Giemsa and counted in a NIKON 80i microscope.

[4] In vivo acute toxicity study: Acute toxicity study was carried out by giving up to 1000 mg/kg dose to uninfected BALB/C mice aged six to eight weeks and weighing 20-22 g. Single dose of 100, 300 and 1000 mg/kg/week were given orally to mice. Mice were observed continuously for one hour after the treatment, on an hourly basis for six hours, and thereafter over a period of 24 h. Several parameters were observed such as weight loses, behavior change, hair erection, reduction in feed and motor activity.

Example 1—Anti-Malarial Activity of Compound I (Calxinin) Assessed by an In Vitro Assay Antimalarial activity of Compound I was assessed in vitro on asynchronous cultures of P. falciparum sensitive (Pf3D7) and chloroquine resistant (PfDd2) clones using a SYBR@ Green assay commercially available from Thermo Fisher Scientific Inc. The mean half maximal inhibitory concentration ($IC_{50}$) values for Pf3D7 and PfDd2 were 90 (±1.9) and 88 (+1.1), respectively. Compound I showed the most potent antiparasitic activity against blood stage parasites, and was more potent against the drug resistant PfDd2 strain.

Example 2—Anti-Plasmodial Activity of Compound I (Calxinin) In Vitro

Antimalarial activity of Compound I was assessed on asynchronous cultures of P. falciparum CQ-sensitive (Pf3D7) and CQ-resistant (Pf Dd2) clones incubated with drugs at 37° C. for 72 hours using the 'SYBR Green I' assay (the mean $IC_{50}$ values are shown in Table 1). As shown in the Table 1, Compound I was equally or more effective against the drug resistant DD2 strain than the other drugs tested.

TABLE 1

| Treatment | Pf3D7 $IC_{50}$, nM (±SD) | PfDd2 $IC_{50}$, nM (±SD) | Field isolates from Kenya $IC_{50}$, nM (±SD) |
|---|---|---|---|
| Chloroquine (CQ) | 32.3(±1.2) | 137(±0.5) | 75.22(±122, n = 131) |
| Dihydroartemisinin (DHA) | 27(±0.6) | 46(±0.6) | 7.37(±12.8, n = 114) |
| Compound I (Calxinin) | 90(±01.9) | 88(±1.1) | 50(±7.2, n = 8) |

Example 3—Compound I (Calxinin) has a Synergistic Effect when Combined with Dihydroartemisinin (DHA)

[5] Compound I was tested in vitro in combination with Dihydroartemisinin (DHA), an antimalarial drug currently in use. For this investigation, fractional inhibitory concentrations (FIC) were applied to determine the drug-drug interactions in killing the parasites. The results are represented in Table 2. Combinations of Compound I with DHA, showed a synergistic effect against in vitro growth of the PfDd2 strain.

TABLE 2

| Drug | ΣFIC5 1:1 | 2:2 | 3:2 | 2:3 | 1:4 | Mean FIC50 | Interaction |
|---|---|---|---|---|---|---|---|
| I + DHA | 0.5 | 0.4 | 0.4 | 0.3 | 0.2 | 0.4 | Synergy |

Example 4—In Vitro Cytotoxicity Assays

[6] PBMC were isolated from healthy donors using the Ficoll-Paque™ technique (GE Healthcare Bioscience AB, Uppsala, Sweden) from donor leukopack samples obtained from LUMC blood bank services. Assessment of the effect of the Calxinin on PBMC cell viability and proliferation, showed that it in fact enhanced PBMC growth (% PBMC viability>100% relative to vehicle control) PBMC was maintained in RPMI 1640 medium supplemented with 10% fetal bovine serum, and Penicillin-streptomycin (1% v,v) (Gibco, UK) at 37° C. Robust cells at a concentration of 80,000 cells/ml were plated into 96-well plates and incubated for 24 hours. Cell viability and proliferation was determined by use of both MTT and Cell Titer Glo@ assays for both cell types. MTT assay was conducted by addition of 10 µL MTT solution (5 mg/mL) into each well, incubated for 4 hour at 37° C. followed by addition of 50 µL DMSO to dissolve the formazan precipitate according to the manufacturer's protocol. Aliquots were drawn from each well and color intensity was measured spectrophotometrically in SpectraMax® M5 Multi-Mode Microplate Reader.

In addition, the cell viability of Huh 7 and HEK293 cells was evaluated post drug exposure using the Alamar Blue assay [Riss, Terry L., et al. "Cell viability assays." Assay Guidance Manual [Intenet]. Eli Lilly & Company and the National Centre for Advancing Translational Sciences, 2016]. Cells (1×10/well) were exposed to varying concentrations of test compounds, for 24 hours in 96-well plate format along with 10/100 µL Alamar Blue solution (10×=4.8 mM in phosphate buffer) per well. Cell viability was measured using the SpectraMax® M5 Multi-Mode Microplate Reader, at 530 nm excitation wavelength and 590 nm emission wavelength for metabolically reduced resazurin dye. Results from the cytotoxicity assays were expressed as $CC_{50}$ at which 50% of the cells died/metabolically slowed down due to drug exposure compared to the non-treated and vehicular control.

Figure 4A:
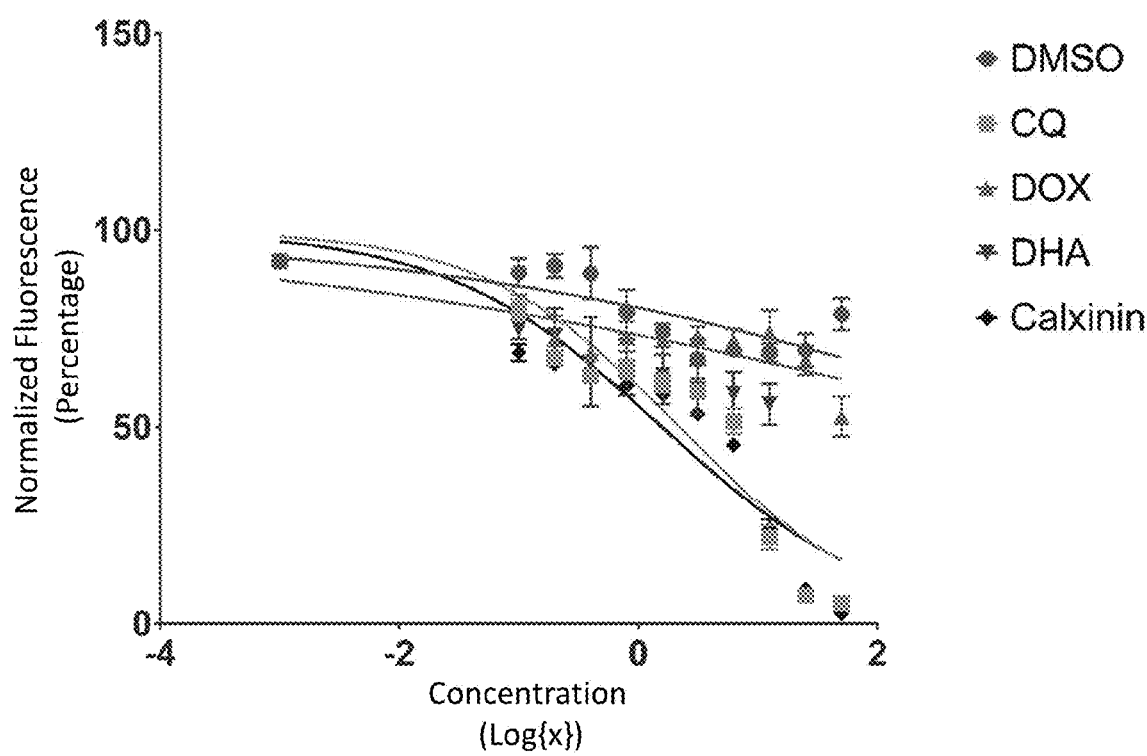
FIG. 4A is a graph showing dose response curves for Calxinin (Compound I (Calxinin)), Chloroquine, DHA, DOX and DMSO (control) in in parasitized RBCs.
Figure 4B:
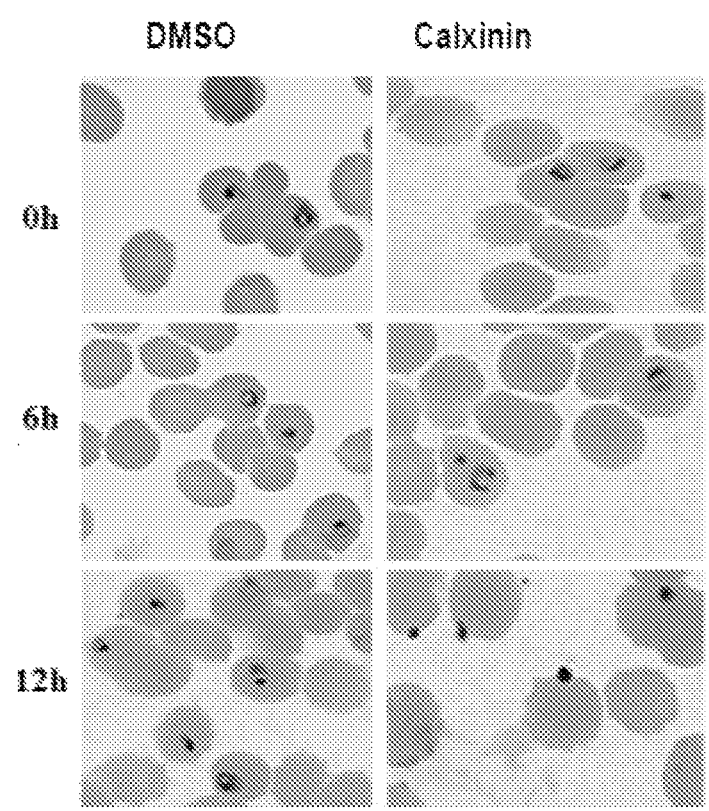
FIG. 4B Micrograph showing ring stage specificity of Compound-I.

The cytotoxicity of Compound I was tested by exposing peripheral blood mononuclear cells (PBMCs) to drug concentrations corresponding to averages of both Pf3D7 and PfDd2 $IC_{50}$ values. This was intended to establish whether the observed antiparasitic effects of the compounds were due to non-specific inhibitory activity. Compound I was observed to enhance proliferation of the PBMCs (PBMC: 110.12: percent inhibition: +3.27) and did not show any toxicity using a cell viability assay (Cell Titer-GLO® reagent). The cytotoxicity of Compound I was also tested by exposing peripheral blood mononuclear cells (PBMC), kidney (HEK293) and liver (Huh 7.1 and HepG2) cells to drug concentrations corresponding to average of both 3D7 and DD2 $IC_{50}$ values. This was to establish if the observed antiparasitic effects of the compounds is due to non-specific inhibitory activity. Calxinin did not show any toxicity to HEK293 (FIG. 4), Huh 7.1, HepG2 and PBMCs as shown in Table 3, below. The $IC_{50}$ required for killing the parasite is <90 nM. Therefore, in order to be toxic for human cells we have to use over 650 fold concentration.

TABLE 3

| Cell Type | $CC_{50}$* (50% cell toxicity) |
|---|---|
| PBMCs | 1000 μM |
| HEK293 | 60.18 μM |
| Huh 7.1 | 100 μM |
| HepG2 | 1350 μM |

*50% cell cytotoxicity

Example 5—Effect of Compound I (Calxinin) in Drug Sensitive Pf3D7 Strain

Initially, antimalarial activity of Compound I was assessed on asynchronous cultures of *P. falciparum* sensitive (Pf3D7) clone using the SYBR Green assay. The mean $IC_{50}$ value is 88 nM. Calxinin showed most potent antiparasitic activity against blood stage parasites in nanomolar concentrations. DMSO was used as a vehicle control, CQ (Chloroquine), DOX (Doxycycline) and DHA (Dihydroartemisinin). After normalizing the signal, Calxinin had the most activity compared to the current STD antimalarial drugs including CQ.

Example 6—Effect of Compound I (Calxinin) on the Artemisinin ("ART") Resistant Field Strain IPC 3445

Figure 5:
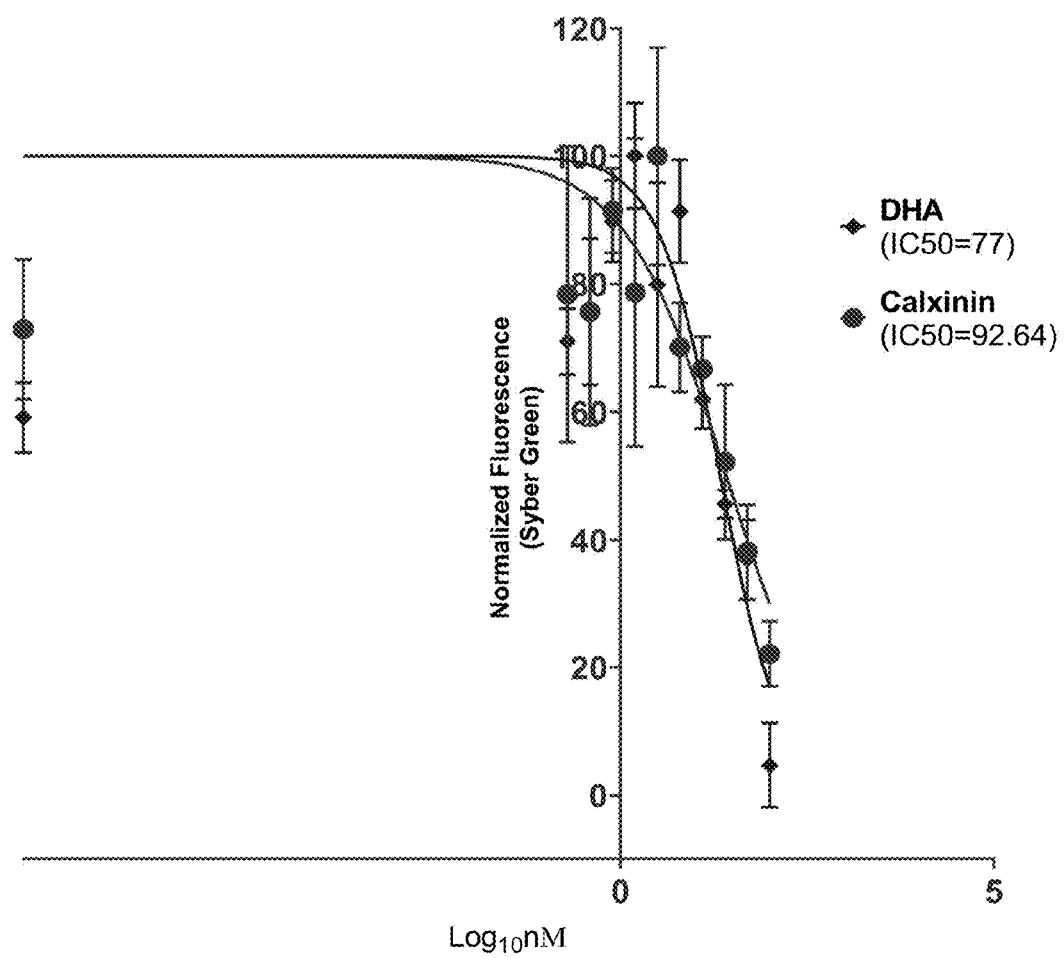
FIG. 5 is a graph showing the anti-malarial activity of Compound I (Calxinin) in dihydroartemisinin (DHA) resistant strain from field.

*Plasmodium falciparum* (*P. falciparum*), strain IPC 3445 was isolated in 2010 from the blood of a human patient with malaria in Pailin province, western Cambodia. Parasites were grown in the lab and tested with different concentrations of the Calxinin and DHA (100 μM-90 nM) for 72 hr incubations. *P. falciparum*, strain IPC 3445 has shown resistance to ART and when exposed to dihydroartemisinin gave a ring-stage survival assay (RSA0-3 h) value of 27.3%. Results show that Calxinin inhibited identical to other strains without any impact of ART resistance, while double the concentration so DHA is required for $IC_{50}$. As shown in FIG. 5, Compound I can inhibit the ART resistant strain with $IC_{50}$ of 92.64 nM.

Figure 1:
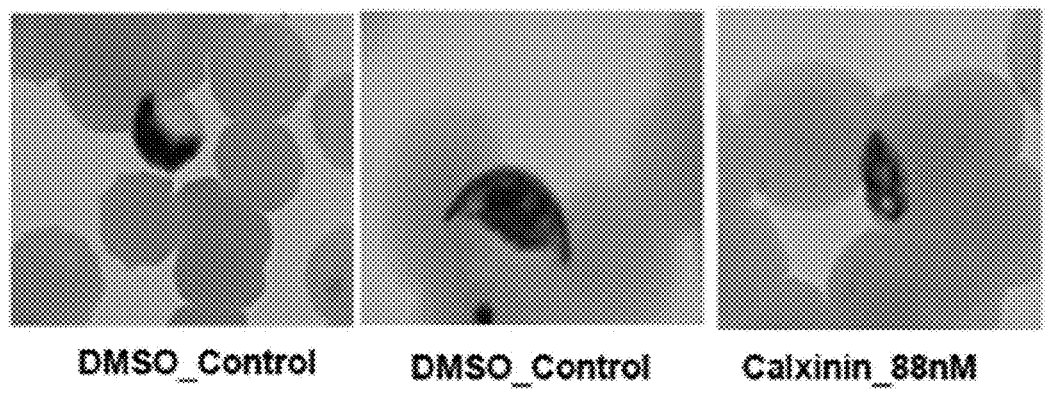

Example 7—Effect of Compound I (Calxinin) on the Development of Sexual Erythrocytic Stages of PfDd2 Cultures The effect of Compound I was tested on the development of sexual erythrocytic stages of PfDd2 cultures. Stage I and II gametocytes, were incubated for forty-eight hours with drug concentration considering the $IC_{50}$ values of compounds at asexual stage assay. This exposure resulted in a decreased maturation of stage III to V gametocytes (PfDd2: 41.0: percent inhibition: ±3.12) and morphologically distorted gametocytes compared to a dimethyl sulfoxide (DMSO) control as shown FIG. 1.

Figure 3:
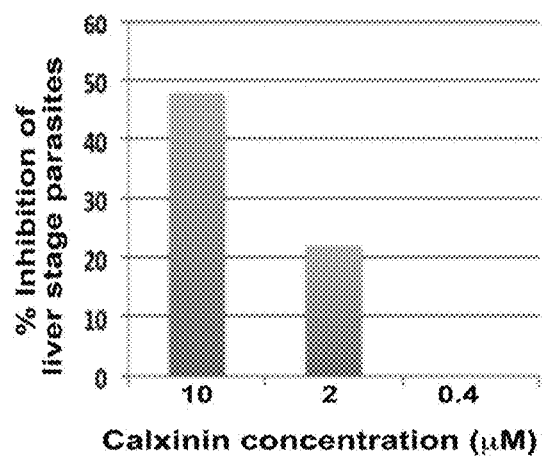

Example 8—Effect of Compound I (Calxinin) Against *Plasmodium* Liver Stage Parasites In Vitro Compound I was tested in vitro against *Plasmodium* liver stage parasites. HepG2 cells, a human hepatocyte cell line, were infected with *Plasmodium* berghie sporozoites (mosquito infective forms of malaria). One set of cells was treated with 0.4, 2.0 and 10.0 micromolar concentration of inhibitor Compound I, and the other set was left untreated. Observed data relating to parasite growth and percent inhibition are shown in FIG. 3. Sporozoite infection time was considered as zero time. Twenty-four hours after infection the culture media was refreshed and the inhibitors were replenished. After forty-eight hours, total cells were harvested and total RNA was extracted by the Trizol™ method. RNA was converted into cDNA and realtime PCR was performed using the parasite 18SrRNA primers. This determined the liver stage parasite burden, which was then converted into percent inhibition by comparing with the untreated set.

Example 9—Compound I (Calxinin) has an Anti-Malarial Effect In Vivo

Figure 2A:
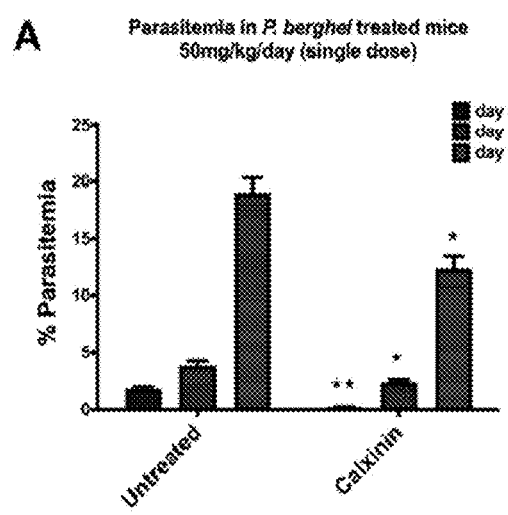
Figure 2B:
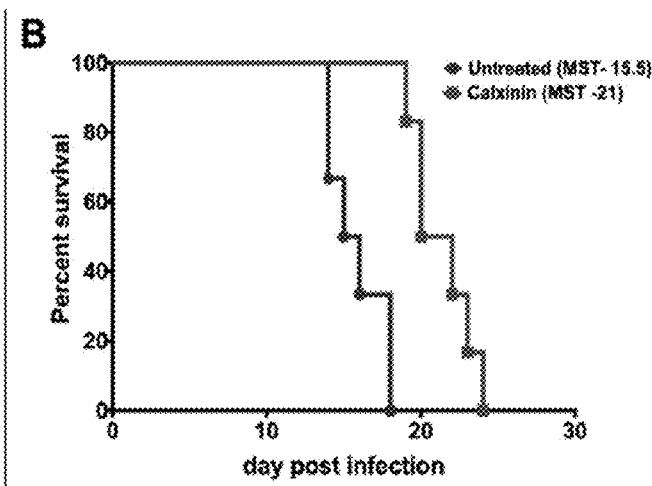

Based on the results of the previously discussed investigations, in vivo animal models were tested to assess the antimalarial activity of Compound I. The antimalarial activity was carried out according to a slightly modified version of the 'Peters four-day suppressive test'. Specifically, a murine model of malaria was developed wherein thirty healthy Swiss albino mice were inoculated intraperitoneally with $1\times10^7$ *Plasmodium berghei* NK-65 (chloroquine-resistant) infected red blood cells (RBCs) suspended in RPMI 1640 medium (commercially available from Thermo Fisher Scientific Inc.; 200 μL). A first set of the infected mice was treated each day with a single dose of 50 mg/kg of Compound I, and a second set was not treated. The survival of the mice was monitored to day 30 post-infection using a Kaplan-Meier survival analysis, and the statistical difference in animal survival was analyzed by a log rank test. Representative data for the percent parasitemia for untreated mice (control) and mice treated with Compound I are shown in Table 4 and FIG. 2A and FIG. 2B.

TABLE 4

| | Percent Parasitemia | | |
|---|---|---|---|
| | Day 3 | Day 7 | Day 10 |
| Untreated | 1.83 | 3.86 | 19.0 |
| Compound I (Calxinin) | 0.21 ** (P < 0.001) | 2.45 * (P < 0.03) | 12.3 * (P < 0.01) |

Example 10—Anti-Gametocyte Activity

Stage I and II gametocytes were incubated for 48 hrs with Compound I (Calxinin) at blood stage $IC_{50}$ ($IC_{50}$, 88 nM). Currently approved anti-malaria drugs have $IC_{50}$ values in the µM range for controlling sexual stage parasites, including the recently approved drug for liver stage "Tafenoquine." Compound I (Calxinin), however, was found to act in the nM range. Treatment with Compound I (Calxinin) resulted in decreased proportion of stage III to V gametocytes (up to 59%) and morphologically distorted gametocytes compared to DMSO control (data not shown).

Example 11—In-Vivo Blood Stage *P. berghei* Mouse Model

Activity of Compound I (Calxinin) was tested using a slightly modified version of Peter's 4-day suppressive test: initial infection of mice with *P. berghei* parasites, followed one dose 50 mg/kg of drug treatment, followed by monitoring of parasitemia as well as external signs of disease progression for up to 10 days. NK64 strain shows significant activity against mixed blood stages at concentrations as low as 50 mg/kg/day (single dose).

$10^7$ *Plasmodium berghei* NK-65 (CQ-resistant) were administered by i.p into Swiss albino mice (6 mice/group). Infected mice were either treated with Compound I (Calxinin) or injected with DMSO alone (untreated vehicle control). Percent parasitemia was determined on days 3, 7 and 10, post infection (**=p<0.001; *=p<0.01) (FIG. 6A and Table 5). The survival of the mice was followed up to day 30 post-infection using Kaplan-Meier survival analysis (FIG. 6B). Animal survival was analyzed by a log rank test.

TABLE 5

| Treatments | % Parasitemia | | |
|---|---|---|---|
| | Day 3 | Day 7 | Day 10 |
| Untreated control | 1.83 | 3.86 | 19 |
| Compound I (Calxinin) | 0.21 ** (P < 0.001) | 2.45 * (P < 0.03) | 12.3 * (P < 0.01) |

Example 12—Liver Stage Assays

Liver schizont stages are the first stage of human infection after injection of sporozoites by mosquitoes. The activity of compounds against this stage offers the important part of the antimalarial therapy, chemoprotection. To evaluate the efficacy of Compound I against liver stage parasites, HepG2 cells were infected with *P. berghei* sporozoites, in triplicates, and dosed with 0.1, 1, 10 µM of Compound I dissolved in 1% DMSO. The parasite load was quantified in control and Compound I-treated cells by quantitative PCR (qPCR) using parasite specific 18SrRNA primers. Approximately, 60% inhibition was noted upon treating cells with Compound I at 0.1 µM, and about 88% inhibition at 1 µM. Inhibitory effect decreases up to 61% while treating cells with 10 µM due to precipitation of compound at higher concentration (FIG. 3). Notably. Compound I showed the high potency with $IC_{50}$ value 79 nM. The liver stage activity of Compound I is much higher over the current treatments, atovaquone (ATQ) in culture.

Prompted by the notable in vitro liver stage activity, mice were infected with sporozoites through mosquito bites to test the efficacy of Compound I on liver stage infection in mouse models. The infected mice were treated with fixed dose of 10 mg/kg for three days. Liver stage *P. berghei* parasites mature into merozoites in about 55 hours. A 30% inhibition was observed at the given dose of 10 mg/kg (FIG. 6A). To understand the pre-patient period and delay, the starting of blood stage parasite infection was monitored after three days post challenge by observing Giemsa stained smears. One day's delay was observed in the prepatent period. Single day delay in blood stage infection corresponds to about 10-fold decrease in liver parasite burden. Experimental mice were kept for survival studies after treatment with Compound 1 (10 mg/kg) and death day was noted.

Control mice had a Mean survival time (MST) of about 6 days, whereas treated mice showed improved MST of about 9 days (FIG. 6B). The percentage of parasitemia remained low until day 7 post-sporozoite challenges.

Example 13—In-vitro Ookinete inhibition assay Encouraged with notable potency against symptomatic asexual blood stage, liver stage, and gametocidal activity, transmission blocking efficacy of Compound I (Calxinin) was evaluated against ookinete. Compound I showed remarkable inhibition against *P. berghei* ookinete development with $IC_{50}$~150 nM in culture (FIG. 7A). As the concentration of Compound I increases, the percentage of healthy parasite is reduced and the % of deformed parasite increases (FIG. 7B). Microscopic images of the healthy, deformed and retarded ookinete are shown in FIG. 7C and FIG. 7D. Two horizontal panels are representative images of the control (healthy) Ookinete (FIG. 7C) and two horizontal panels are representative images of the deformed and retarded Ookinete resulted from Calxinin treatment at 450 nanomolar concentration (FIG. 7D).

The deformed and retarded parasite cannot continue the cycle, unable to form oocyst for further infection. Overall. Compound I showed high potency to inhibit the oocyst formation and hence capability to block the transmission stages.

Example 14—Effect of Compound I (Calxinin) on Homeostasis In Vitro

Studies were performed to assess the effect of Calxinin on hemostatic parameters using plasmatic and whole blood assays. When added at concentrations up to 20 µg/ml, Calxinin did not impact clot formation as assessed by thrombelastography and did not alter agonist-induced aggregation of human platelets, suggesting that this compound does not have any effect on blood clotting and platelet aggregation. There was no adverse impact of Compound I (Calxinin) on hemostatic parameters: (FIGS. 8A-8C) anticoagulant effect; (FIG. 8D) clot formation: and (FIG. 8E, FIG. 8F) agonist-induced aggregation of human platelets (20 µg/ml).

Example 15—Compound I (Calxinin) Target Validation

Patch Clamp to measure non-specific interaction of Calxinin with host calcium channel. To vary this, HEK 293 cells constitutively expressing human T-type calcium channel were used to measure the change in the current upon adding Calxinin. These currents were measured with the Patch clamp method in the "whole cell" configuration. In this configuration, the total currents that pass through all the calcium channels present in the plasma membrane are measured. In this case, it is measured in HEK cells, which constitutively express the human T type Calcium channel. In this case, the internal solutions contain the Cs+ instead of K+, thus blocking the K+ channels and the external one contains TEA an external channel blocker of K. This way the only currents that can develop in these cells are that of T type Calcium channels. This calcium channel is a voltage dependent channel, which is characterized by activating at membrane potentials that are more negative than L-type channels and by rapidly inactivating. It can be seen that at negative membrane potentials (−100, −80, −60 mV) no current develops. At potential of −50 mV the development of a current is clearly observed and as the membrane potential becomes less negative (−40, −20, 0, +20 +30 mV) the current developed is getting smaller, the reason of this behavior is: because when the membrane potential becomes less negative, the T type Calcium channel becomes activated! And very quickly they inactivates and therefore are not able to conduce Ca current, this makes the total currents smaller. This is the characteristic of the human T type calcium channel.

No difference in the activity of the Calcium T Channel was observed under control conditions and with increasing concentrations of the Calxinin molecule, there is no difference in the amplitude of the calcium channel currents, nor in the dependence with the membrane potential of calcium channel activation up to 1 microMolar, that is 20 fold higher than the IC50 to kill the parasite. Human T-type calcium channel currents were measured with the Patch clamp on the "whole cell" configuration in HEK cells constitutively expressing human T type Calcium channel. No difference was observed in the activity of the Calcium T Channel under DMSO treated and with increasing concentrations of the Compound I (Calxinin). As shown, in FIG. 9 no difference in the amplitude of the calcium channel currents, nor in the dependence with the membrane potential of calcium channel activation even at 11 times the $IC_{50}$ concentration. Preliminary results of parasitized RBC treated with CQ (I0 µM)+ DMSO (negative control) and treated Compound I (10 µM, data not shown) were generated. Treatment of Compound I resulted in changes in the calcium levels of packed red blood cells (pRBCs) within a few seconds.

Example 16—Anti-*Leishmania* Effect of Compound I (Calxinin)

To test the anti-*leishmania* activity, *Leishmania donovani* strains: *L. donovani* reporter expressing red fluorescent protein, DsRed2 transgenic *L. donovani* (LV82)15, obtained from Ohio State University. Columbus (OSUMC). Extracellular (Promastigotes) *L. donovani* parasites were maintained in M199 media supplemented with 15% heat-inactivated fetal bovine serum (HI-FBS), 20 mM HEPES, 100 U/ml of penicillin and streptomycin at pH 5.5 with 5% $CO_2$. Cultures were constantly maintained in a 25° C. incubator. Anti-leishmanial activity was determined by incubating exponentially growing log-phase promastigotes with THP-1 macrophage for 24 h to infect. Following this, plates were washed to remove the uninfected promastigotes, STD drug and Calxinin were treated 96-well plates for 96 hours. Miltefosine and paromomycin, standard medications, serve as a positive control at equivalent concentrations. Morphological alterations in the amastigotes following treatment with drugs, were examined by fluorescent microscopy. Images were analyzed for percent parasite survival upon drug treatment and enumerated the $IC_{50}$. The dose response curves of *Leishmania* donovani amastigotes stages are shown in FIG. 13. The inhibition curve of Compound I was very similar to Amphotericin B (AmpB) and lower than the 2 standard drugs. The $IC_{50}$ of Compound I was determined to be 79.84 nM.

Example 17—Monitoring Calcium Levels in *L. donavani* Infected THP1 Cells

A macrophage differentiated cell culture of THP1 cell lines by phorbol 12-myristate 13-acetate (PMA) concentration of 15 ng/ml was established on 15 mm glass bottom petri dishes. The confluent cells were infected with *leishmania* promastigotes in 1:5 ratio. The infected macrophages were washed after 24 hr.

Incubation was conducted to remove uninfecting promastigotes with same RPMI medium with 6% FCS. The culture was then washed twice in HEPES-buffered saline solution (HBSS) (in mM: 25 HEPES, 121 NaCl, 5 $NaHCO_3$, 4.7 KCl, 1.2 $KH_2PO_4$, 1.2 $MgSO_4$, 2.0 $CaCl_2$), 10 glucose, 0.04 probenecid, and 0.25% (w/v) fatty acid-free BSA, pH 7.4). The culture was switched to the same buffer with Fluo4-AM (1×), Hoechst 33258 (1×) and charged for 40 minutes. The cells were then washed in same buffer without dye and mounted on the stage of inverted LSM 510 Zeiss, 10×, 1.4 NA, oil-immersion objective, zoom 4-6, z-stacks of 0.7-µM thin optical sections, 4-8× average, 2,000×2,000 pixel window, range indicator used for optimized illumination, and 488, 543, 633 laser lines used for excitation. Compounds Miltefosine, Amphotericin B, calxinin and DMSO were added during time-course experiments. Preliminary results of Amastigotes treated with DMSO (negative control) and treated Compound 1 (10 µM) were generated.

Treatment of Compound I resulted in changes in the calcium levels of Macrophage+*L. donavani* within few seconds (data not shown).

Example 18—Toxicity Evaluation in Mice: Pathological Examination

Testing of acute toxicity study: Administration of Compound I (Calxinin) or 0.2 ml of vehicle (10% DMSO in PBS) was performed by oral gavage at a dose of 300 mg/kg for four consecutive days as follows. Calxinin was evaluated for its toxicity in Balb C mice aged six to eight weeks and weighing 20-22 g. Mice were divided in into two groups of three mice. Before oral administration of a single dose of compound, the mice were fasted for one or two hours. Then, the mice in group I were given orally 0.2 ml of vehicle (10% DMSO in PBS) and the remaining mice were given a single dose of 100, 300 and 1000 mg/kg/week orally. Then the mice were observed continuously for one hour after the treatment, intermittently for six hours, and thereafter over a period of 24 hours. Several parameters were observed such as weight loses, behavior change, hair erection, reduction in feed and motor activity. Again mice were randomly divided in two groups. Each group consisted of 3 mice. Administration of calxinin was performed by oral gavage at a dose of 300 mg/kg for four consecutive days. Animals were sacrificed at the end of experiment by cervical dislocation. Histopathology: Mice were sacrificed by cervical dislocation, their livers, kidney and stomach were extracted and fixed in 10% formalin for 24 hours. Finally the samples embedded in paraffin and fine sections were stained with hematoxiline-eosine. Animal treatments were performed following CPCEA regulations at National Institute of Immunology, New Delhi. Six-week-old BALB/C mice were housed at 22±2° C. with a 12-h light/dark cycle and fed standard rodent chow and water ad libitum.

Acute toxicity study: Calxinin was evaluated for its toxicity in Balb/C mice aged six to eight weeks and weighing 20-22 g. Mice were divided into two groups of three mice. Before oral administration of a single dose of compound, the mice were fasted for one or two hrs. Then, the mice in the group 1 were given orally 0.2 ml of vehicle (10% DMSO in PBS) and the remaining mice were given a single dose of 100, 300 and 1000 mg/kg/week orally. Then the mice were observed continuously for one hr after the treatment, intermittently for six hrs, and thereafter over a period of 24 hrs. Several parameters were observed such as weight loses, behavior change, hair erection, reduction in feed and motor activity. Again Mice were randomly divided in two groups. Each group consisted of 3 mice. Administration of calxinin was performed by oral gavage at a dose of 300 mg/kg for four consecutive days. Animals were sacrificed at the end of experiment by cervical dislocation. The liver, kidney and stomach were isolated and let them fixed in formalin. Routine (H&E) staining was done and slides were visualized in microscope. Serum was taken for biochemistry studies.

Results demonstrated that no indication of acute toxicity in the mice as their weight remained constant. Further, no behavior changes were observed. Motor and feeding activities were normal. Pathological examination of the major organs of the mice in the Compound 1 (Calxinin)-treated groups does not indicate an increase or decrease of Kuepfer cells in the liver, loss of structural integrity in the kidney or lining of stomach. Overall there is no indication of toxicity by Compound I (Calxinin) at 1200 mg/kg (300 mg/kg was given for four consecutive days) (data not shown). Biochemical examination of liver and kidney function was also performed, the results of which are shown in Table 6 below.

TABLE 6

| Serum Analytes | Mice injected with vehicle | Mice injected with Compound I (Calxinin) | Reference Ranges |
| --- | --- | --- | --- |
| Bilirubin | 0.29 mg/dL | 0.28 mg/dL | 0.5-1.0 |
| Total protein | 6.91 g/dL | 6.56 g/dL | 5.6-7.6 |
| Albumin | 3.82 g/dL | 3.77 g/dL | 3.8-3.1 |
| Globulin | 3.09 g/dL | 2.79 g/dL | 1.8-3.1 |
| ALP | 196 U/L | 157 U/L | 45-178 |
| AST | 405 U/L | 178 U/L | 54-298 |
| ALT | 98 U/L | 64 U/L | 17-77 |
| Urea | 98 mg/dL | 112 mg/dL | 15-68 |

TABLE 6-continued

| Serum Analytes | Mice injected with vehicle | Mice injected with Compound I (Calxinin) | Reference Ranges |
| --- | --- | --- | --- |
| Creatine | 1.12 mg/dL | 1.65 mg/dL | 0.5-1 |
| Uric acid | 2.16 mg/dL | 2.56 mg/dL | 1.5-3.2 |

The foregoing description is given for clearness of understanding only, and no unnecessary limitations should be understood therefrom, as modifications within the scope of the invention may be apparent to those having ordinary skill in the art.

Throughout this specification and the claims which follow, unless the context requires otherwise, the word "comprise" and variations such as "comprises" and "comprising" will be understood to imply the inclusion of a stated integer or step or group of integers or steps but not the exclusion of any other integer or step or group of integers or steps.

Throughout the specification, where compositions are described as including components or materials, it is contemplated that the compositions can also consist essentially of, or consist of, any combination of the recited components or materials, unless described otherwise. Likewise, where methods are described as including particular steps, it is contemplated that the methods can also consist essentially of, or consist of, any combination of the recited steps, unless described otherwise. The invention illustratively disclosed herein suitably may be practiced in the absence of any element or step which is not specifically disclosed herein.

The practice of a method disclosed herein, and individual steps thereof, can be performed manually and/or with the aid of or automation provided by electronic equipment. Although processes have been described with reference to particular embodiments, a person of ordinary skill in the art will readily appreciate that other ways of performing the acts associated with the methods may be used. For example, the order of various of the steps may be changed without departing from the scope or spirit of the method, unless described otherwise. In addition, some of the individual steps can be combined, omitted, or further subdivided into additional steps.

All patents, publications and references cited herein are hereby fully incorporated by reference. In case of conflict between the present disclosure and incorporated patents, publications and references, the present disclosure should control.

We claim:

1. A compound having a structure of formula (I):

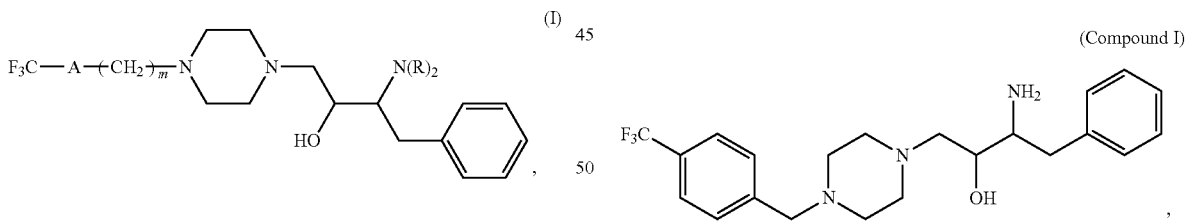

or a pharmaceutically acceptable salt thereof, wherein:
A is $C_{6-10}$ aryl;
each R independently is or $CH_3$; and
m is 1, 2, or 3.

2. The compound or salt as claimed in claim 1, wherein A is phenyl or naphthyl.

3. The compound or salt as claimed in claim 2, wherein A is phenyl.

4. The compound or salt as claimed in claim 1, wherein each R independently is H.

5. The compound or salt as claimed in claim 1, wherein m is 1.

6. The compound salt as claimed in claim 1, wherein m is 2.

7. The compound or salt as claimed in claim 1, wherein m is 3.

8. The compound as claimed in claim 1, having a (Compound I)

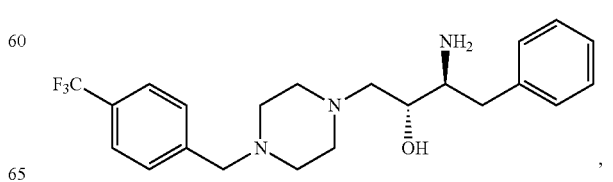

Structure or a pharmaceutically acceptable salt thereof.

9. The compound as claimed in claim 8, having a structure (Compound Ia)

or a pharmaceutically acceptable salt thereof.

10. A pharmaceutical composition comprising:
the compound or salt as claimed in claim 1; and a pharmaceutically acceptable excipient.

11. A method of treating a protozoan parasitic disease in a subject comprising:
administering, to the subject, a therapeutically effective amount of a compound having a structure of formula (I):

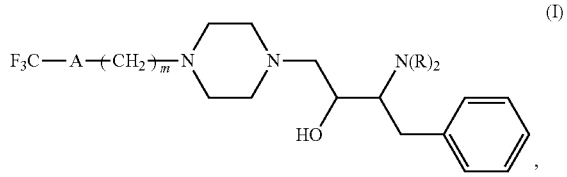

or a pharmaceutically acceptable salt thereof, wherein:
A is $C_{6-10}$aryl;
each R independently is H or $CH_3$; and
m is 1, 2, or 3.

12. The method of claim 11, wherein the protozoan parasitic disease is malaria, Leishmaniasis, Toxoplasmosis, Chagas, or Cryptosporidiosis.

13. The method as claimed in claim 11, wherein the protozoan parasitic disease is malaria, and
the malaria is liver stage malaria; blood stage malaria; or gametocyte and/or ookinete stage malaria.

14. The method as claimed in claim 11, wherein
the protozoan parasitic disease is Leishmaniasis;
the subject is infected with a Leishmaniasis-causing parasite; and
the Leishmaniasis-causing parasite is *Leishmania* that is *donovani*, *Leishmania major*, *Leishmania tropica*, *Leishmania braziliensis*, *Leishmania mexicana*, *Leishmania amazonensis*, or *Leishmania Chagasi*.

15. The method as claimed in claim 11, wherein
the protozoan parasitic disease is Toxoplasmosis; and
the subject is infected with a Toxoplasmosis-causing parasite that is *Toxoplasma gondii*.

16. The method as claimed in claim 11, wherein the protozoan parasitic disease is Chagas;
wherein the subject is infected with a Chagas-causing parasite that is *Trypanosoma cruzi*.

17. The method as claimed in claim 11, wherein
the protozoan parasitic disease is Cryptosporidiosis,
the subject is infected with a Cryptosporidiosis-causing parasite, and
the Cryptosporidiosis-causing parasite is *Cryptosporidium parvum* and *Cryptosporidium hominis*.

18. The method as claimed in claim 11, wherein the compound is administered in combination with another anti-parasitic therapeutic, and
wherein the other anti-parasitic therapeutic is selected from the group consisting of quinine, chloroquine ("CQ"), proguanil, sulfadoxine-pyrimethamine, mefloquine, atovaguone, doxycycline ("DOX"), clindamycin, artemisinin, and dihydroartemisinin ("DHA").

19. The method as claimed in claim 18, wherein the other anti-parasitic therapeutic is dihydroartemisinin ("DHA").

* * * * *